(12) United States Patent
Miyabe et al.

(10) Patent No.: US 6,342,248 B1
(45) Date of Patent: *Jan. 29, 2002

(54) DIVIDABLE TABLET AND PRESS-THROUGH PACK

(75) Inventors: Junichi Miyabe, Susono; Kiyoshi Morimoto, Mishima; Yuji Iwase, Gotemba; Shigemitsu Miura, Susono; Eiji Hayakawa; Kunio Ito, both of Shizuoka, all of (JP)

(73) Assignee: Kyowa Hakko Kogyo Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/285,062

(22) Filed: Apr. 2, 1999

(30) Foreign Application Priority Data

Apr. 3, 1998 (JP) ............................................ 10-091746

(51) Int. Cl.$^7$ .................................................. A61K 9/44
(52) U.S. Cl. ........................ 424/467; 424/464; 206/532; 206/539
(58) Field of Search ................................ 424/464, 467; 206/539, 532

(56) References Cited

U.S. PATENT DOCUMENTS

| | | | | |
|---|---|---|---|---|
| 3,921,805 A | * | 11/1975 | Compere | 206/532 |
| 4,353,887 A | * | 10/1982 | Hess et al. | 424/15 |
| 4,824,677 A | * | 4/1989 | Shah et al. | 424/467 |
| 5,560,490 A | * | 10/1996 | Chawla | 206/539 |

FOREIGN PATENT DOCUMENTS

| | | |
|---|---|---|
| DE | 296 17 001 | 9/1997 |
| GB | 1 387 643 | 1/1972 |
| GB | 1 368 574 | 10/1974 |
| JP | 61-287568 | 12/1986 |
| JP | 61-289027 | 12/1986 |
| JP | 7-149367 | 6/1995 |
| JP | 7-179333 | 7/1995 |
| JP | 7-257639 | 10/1995 |
| JP | 8-53345 | 2/1996 |
| JP | 8-277217 | 10/1996 |
| JP | 8-277218 | 10/1996 |
| JP | 9-52313 | 2/1997 |
| WO | WO99/18008 | 4/1999 |

* cited by examiner

*Primary Examiner*—Thurman K. Page
*Assistant Examiner*—Liliana Di Nola-Baron
(74) *Attorney, Agent, or Firm*—Fitzpatrick, Cella, Harper & Scinto

(57) ABSTRACT

A dividable tablet is not chipped, can be divided easily and accurately, has excellent impact resistance and rarely causes twining in the film-coating step, wherein a dividing line is formed along a center line on the upper surface of the tablet, ridgelines are each located on an inner side of the peripheral portion of the tablet to surround the dividing line in two areas defined by the dividing line on the upper surface of the tablet, the lower surface of the tablet gradually rises from the peripheral portion of the tablet toward the center portion thereof, and areas around the ridgelines are each formed by a convex surface.

18 Claims, 21 Drawing Sheets

DIVIDABLE TABLET AND PRESS-THROUGH PACK

BACKGROUND OF THE INVENTION

1. Field of the Invention

The present invention relates to a dividable tablet and to a press-through pack and, more specifically, to a dividable tablet which can be divided easily and accurately without being chipped and has excellent impact resistance and such a shape that does not cause the twining of the tablets in the film-coating step and to a press-through pack for containing the same which enables the dividable tablets contained therein to be divided into two easily and simply while they are contained in the press-through pack and all the divided tablets to be taken out at a time.

2. Description of the Related Art

A dividable tablet is divided by a pharmacist at the time of preparation according to dosage or by a patient himself when he takes it and has been developed to optimize the management of dosage for each individual patient and improve prescription ease.

A dividing line (dividing groove) is generally formed in this dividable tablet to divide the tablet.

FIGS. 13A, 13B and 13C are schematic diagrams of a flat dividable tablet of the prior art. FIG. 13A is a plan view, FIG. 13B is a bottom view and FIG. 13C is a side view.

This flat dividable tablet Te has a flat upper surface Sa and a flat lower surface Sb and a dividing line Ld is formed on the upper surface SA along a center line thereof.

To divide the dividable tablet Te into two, two areas R1 and R2 defined by the dividing line Ld on the upper surface Sa are held with the fingers of a pharmacist, patient or the like directly and the dividable tablet Te is divided along the dividing line Ld by spreading wide the dividing line Ld.

However, the dividable tablet Te shown in FIGS. 13A to 13C has such a problem that great force is needed to divide it into two so that it is difficult for a person of advanced age who suffers from a reduction in the strength of his fingers and a reduction in sensibility to divide the dividable tablet Te.

FIGS. 14A to 14C are schematic diagrams of a KARATE SHAPE dividable tablet of the prior art disclosed by Japanese Patent Application Laid-open No. Sho 61-289027. FIG. 14A is a plan view, FIG. 14B is a bottom view and FIG. 14C is a side view.

The KARATE shape tablet Tf has a flat lower surface Sb. A dividing line Ld is formed on an upper surface Sa along a center line thereof and two areas R1 and R2 defined by the dividing line Ld on the upper surface Sa have an inclined plane surface which ascends from lines Ld2 and Ld2 which are the borders of the dividing line Ld toward the periphery of the tablet so that the thickness of the tablet increases toward the periphery of the tablet.

To divide the dividable tablet Tf into two, a pharmacist, patient or the like holds the two areas R1 and R2 with fingers directly and divides it into two along the dividing line Ld. Alternatively, the dividable tablet Tf can be divided into two by placing the tablet upside down and pressing it down from above.

A tablet may contain a component having unpleasant smell or taste or a component which has poor stability against light or the like as an effective ingredient. A tablet containing such an effective ingredient is generally coated with a film to mask the unpleasant smell or taste of the effective ingredient or ensure stability against light or the like.

However, as the dividable tablet Te of the prior art has a flat upper surface Sa and a flat lower surface Sb, the tablets Te are easily face contacted to each other. As a result, in the step of coating a film on the surface of the tablet Te, there easily occurs such a phenomenon (so called twining) that the tablets Te are adhered to each other.

Similarly, as the two areas R1 and R2 defined by the dividing line Ld on the upper surface Sa of the dividable tablet Tf of the prior art are formed by a plane surface and the lower surface Sb also is formed by a plane surface, the tablets Tf are easily face contacted to each other. Therefore, when the surface of the tablet Tf is coated with a film, the phenomenon (so called twining) that the tablets Tf are adhered to each other easy occurs in the film-coating step.

When the dividable tablets Te and Tf of the prior art are coated with a film, the strength of each of the tablets increases by film coating, whereby greater force is needed to divide the tablets or division readily becomes non-uniform.

A dividable tablet that is free from twining in the film-coating step when the tablet is coated with a film and is easily divided into two is already proposed by Japanese Patent Application Laid-open No. Hei 8-53345.

FIGS. 15A to 15C are schematic diagrams of an example of a dividable tablet disclosed by Japanese Patent Application Laid-open No. Hei 8-53345. FIG. 15A is a plan view, FIG. 15B is a bottom view and FIG. 15C is a side view.

A dividing line Ld is formed in this dividable tablet Tg on an upper surface Sa along a center line thereof, two areas R1 and R2 defined by the dividing line Ld on the upper surface Sa have an inclined plane surface from lines Ld2 and Ld2 which are the borders of the dividing line Ld toward the periphery of the tablet so that the thickness of the tablet increases toward the periphery of the tablet, and the lower surface Sb of the tablet Tg has such convexity that a center portion C is higher than a peripheral portion E.

Since the lower surface Sb of this dividable tablet Tg has such convexity that the center portion C is higher than the peripheral portion E, the tablets Tg are point contacted to each other rather than face contacted to each other in many cases. Therefore, twining hardly occurs in the film-coating step.

To divide the tablet Tg into two, a pharmacist, a patient or the like holds the two areas R1 and R2 directly with his fingers and divides it into two along the dividing line Ld. Alternatively, the tablet Tg can be divided into two by pressing it down from above.

FIGS. 16A to 16C are schematic diagrams of another example of a dividable tablet disclosed by Japanese Patent Application Laid-open No. Hei 8-53345. FIG. 16A is a plan view, FIG. 16B is a bottom view and FIG. 16C is a side view.

A dividing line Ld is formed in this dividable tablet (upper KARATE shape and lower standard concave tablet) Th on an upper surface Sa along a center line thereof, two areas R1 and R2 defined by the dividing line Ld on the upper surface Sa have such concavity that the thickness thereof increases from lines Ld2 and Ld2 which are the borders of the dividing line Ld toward the periphery E of the tablet Th, and the lower surface Sb of the tablet Th has such convexity that a center portion C is higher than a peripheral portion E.

Since the lower surface Sb of this dividable tablet Th has such convexity that the center portion C is higher than the peripheral portion E like the dividable tablet Tg, the tablets Th are point contacted to each other rather than face contacted to each other.

Further, as the two areas R1 and R2 defined by the dividing line Ld on the upper side have convexity to eliminate a flat portion from the surfaces of the tablet Th, twining more hardly occurs in this dividable tablet Th than the dividable tablet Tg during the film-coating step.

To divide the tablet Th into two, a pharmacist, patient or the like holds the two areas R1 and R2 directly with his fingers and divides it into two along the dividing line Ld. Alternatively, the tablet Th can be divided into two by pressing it down from above.

The tablet is generally contained in a press-through pack (generally called "PTP") to protect it from moisture, dust, mold, bacteria and the like while it is preserved.

FIG. 17 is a sectional view showing a typical example of the press-through pack.

This press-through pack 101 comprises a storage body 102 and a sealing sheet 103.

The storage body 102 is made from a synthetic resin such as polyvinyl chloride, polypropylene or cyclic polyolefin and has a plurality of storage recessed portions 102b, . . . , 102b which are formed according to the shape of the tablet T and connected by plate portions 102a, . . . , 102a.

The sealing sheet 103 consists of a base 105 made of aluminum foil or the like and an adhesive layer 104 formed on one side of the base 105.

The press-through pack 101 is constituted such that the adhesive layer 104 of the sealing sheet 103 is bonded to the plate portions 102a, . . . , 102a of the storage body 102 to seal the storage body 102 with the sealing sheet 103 while the tablets T, . . . , T are each contained in the storage recessed portions 102b, . . . 102b.

When projecting portions 102c, . . . , 102c which are the exterior sides of the storage recessed portions 102b, . . . 102b of the storage body 102 are each pressed, portions r1, . . . , r1 of the sealing sheet 103 sealing the storage recessed portions 102b, . . . , 102b are broken by the tablets T, . . . , T contained in the storage recessed portions 102b, . . . , 102b so that the tablets T, . . . , T can be taken out from the press-through pack 101 one by one.

When the dividable tablets Te or Tf are contained in this press-through pack 101, a pharmacist or a patient generally breaks the sealing sheet 103 by the dividable tablets Te or Tf contained in the storage recessed portions 102b, . . . , 102b to take out the dividable tablets Te or Tf one by one and then divides the dividable tablets Te or Tf into two with his fingers if necessary.

Japanese Patent Application Laid-open No. Hei 8-53345 teaches that when the dividable tablets Tg or Th are contained in the press-through pack 101, the dividable tablets Tg or Th can be each divided into two before they are taken out from the press-through pack 101.

Thus, if the dividable tablets Tg or Th are each divided into two before they are taken out from the press-through pack 101, it is not necessary to hold the dividable tablet Tg or Th with fingers when it is divided into two. Thereby, when the dividable tablet Tg or Th is divided into two, the tablet Tg or Th is not contaminated with fingers.

However, it cannot be said that such problems that it is difficult to divide the dividable tablet Tg or Th into two by applying force from above in a vertical direction and that defective products are easily produced in the tabletting step or the coating step are completely solved. Further, when the dividable tablet Tg or Th is pneumatically transported from one place to another or transported in the press-through pack 101 or a bottle, it is easily chipped during transportation.

For example, when the dividable tablet Tg is divided by applying force from above in a vertical direction (see FIG. 18A), as shown in FIG. 18B, since the edge portion Pe of the upper surface Sa of the tablet Tg is pointed, force is concentrated on the pointed edge portion Pe and the edge portion Pe may be crushed or chipped.

The dividable tablet Tg has such a problem that the pointed edge portion Pe thereof is easily capped in the tabletting step.

Since the two areas R1 and R2 defined by the dividing line Ld on the upper surface Sa of the tablet Tg are flat, when the area R1 of one tablet Tg is contacted to the area R1 of another tablet Tg, the area R1 of one tablet Tg is contacted to the area R2 of another tablet, or the area R2 of one tablet Tg is contacted to the area R2 of another tablet Tg, the tablet Tg is face contacted to the tablet Tg. In this case, since the tablets Tg are face contacted to each other, such a problem that twining occurs in the coating step cannot be solved yet.

Since the edge portion Pe on the upper surface Sa of the tablet Tg is pointed, core erosion (phenomenon in which original tablet abrades), edge chipping (phenomenon in which edge portion is chipped) or the like readily occurs by collision between the tablets Tg.

When the tablet Tg is pneumatically transported from one place to another, there are such problems that the edge portion Pe on the upper surface Sa of the tablet Tg may be chipped by collision between the tablets Tg or collision between the tablet Tg and a transport pipe during pneumatically transportation and that the edge portion Pe on the upper surface Sa of the tablet Tg may be chipped or the sealing sheet 103 is broken with the edge portion Pe by collision between the pointed edge portion Pe and the storage body 102 or the sealing sheet 103 due to vibration produced during transportation when the tablet Tg is transported in the press-through pack 101.

When the tablets Tg are contained in a bottle, the edge portion Pe may be chipped by collision between the tablets Tg or collision between the tablet Tg and the bottle due to vibration produced during transportation.

Further, when the tablet Tg is contained in the press-through pack 101 and the upper surface Sa having the dividing line Ld of the tablet Tg contained in the storage recessed portion 102b of the storage body 102 of the press-through pack 101 faces the sealing sheet 103 (see the tablet Tg contained in the storage recessed portion 102a on the right side of FIG. 19A), the tablet Tg can be divided into two easily by pressing the protuberant center portion of the lower surface Sb of the tablet Tg through a projecting portion 102c which is the exterior surface of the storage recessed portion 102b of the storage body 102 of the press-through pack (see the tablet Tg contained in the storage recessed portion 102b on the right side of FIG. 19B). Conversely, when the upper surface Sa having the dividing line Ld of the tablet Tg contained in the storage recessed portion 102b of the storage body 102 of the press-through pack 101 faces the storage body 102 (see the tablet Tg contained in the storage recessed portion 102b on the left side of FIG. 19A), relatively large force is needed to divide the tablet Tg into two because, when the projecting portion 102c which is the exterior surface of the storage recessed portion 102b of the storage body 102 of the press-through pack 101 is pressed with a finger, the two areas R1 and R2 defined by the dividing line Ld on the upper surface Sa of the tablet Tg take the same form as the storage recessed portion 102b crushed substantially into a V shape when seen from side and the finger.

Therefore, to make it easy to divide the tablet Tg into two before taking out the tablet Tg from the storage recessed portion 102b of the storage body 102 of the press-through pack 101, as shown on the right side of FIG. 19A, the directions of all the tablets Tg to be contained in the storage recessed portions 102b of the storage body 102 of the press-through pack 101 must be limited such that the upper surfaces Sa having the dividing line Ld of the tablets Tg face the sealing sheet 103. It is extremely difficult to contain all the tablets in the storage recessed portions 102b of the storage body 102 of the press-through pack 101 while they are limited to a certain direction.

Even if all the tablets Tg can be contained in the storage recessed portions 102b of the storage body 102 of the press-through pack 101 while they are limited to a certain direction, when the tablets Tg are each contained in the storage recessed portions 102 in such a manner that the upper surfaces Sa having the dividing line Ld of the tablets Tg face the sealing sheet 103, the pointed edge portion Pe faces the sealing sheet 103, whereby the sealing sheet 103 is easily broken by the pointed edge portion Pe without being pressed with a finger.

When the dividable tablet Th is to be divided by applying force from above in a vertical direction like the dividable tablet Tg (see FIG. 20A), there are such problems that force is concentrated on the pointed edge portion Pe and the edge portion Pe is thereby crushed or chipped as the edge portion Pe of the upper surface Sa of the tablet Th is pointed, thereby making it difficult to divide the dividable tablet Th (see FIG. 20B) and that the pointed edge portion Pe is easily capped in the tabletting step.

Since the edge portion Pe of the upper surface Sa of the tablet Th is pointed, core erosion (phenomenon in which original tablet abrades) or edge chipping (phenomenon in which edge portion is chipped) readily occurs due to collision between the tablets Th in the coating step like the dividable tablet Tg.

Further, when the tablets Th are pneumatically transported from one place to another, the edge portion Pe of the upper surface Sa of the tablet Th may be chipped by collision between the tablets Th or collision between the tablet Th and a transport pipe during transportation. When the tablets Th are transported in the press-through pack 101, the edge portion Pe of the upper surface Sa of the tablet Th may be chipped by their collision with the storage body 102 or the sealing sheet 103, or the sealing sheet 103 may be broken by the edge portion Pe due to vibration produced during transportation. When the tablets Th are contained in a bottle, the edge portion Pe may be chipped by collision between the tablets Th or collision between the tablet Th and the bottle due to vibration produced during transportation.

Further, when the tablets Th are contained in the press-through pack 101 and the upper surface Sa having the dividing line Ld of the tablet Th contained in the storage recessed portion 102b of the storage body 102 of the press-through pack 101 faces the sealing sheet 103 (see the tablet Th contained in the storage recessed portion 102b on the right side of FIG. 21A), the tablet Th can be easily divided into two by pressing the protuberant center portion of the lower surface Sb of the tablet Th through the projecting portion 102c which is the exterior surface of the storage recessed portion 102b of the storage body 102 of the press-through pack 101 (see the tablet Th contained in the storage recessed portion 102b on the right side of FIG. 21B). Conversely, when the upper surface Sa having the dividing line Ld of the tablet Th contained in the storage recessed portion 102b of the storage body 102 of the press-through pack 101 faces the storage body 102 (see the tablet Th contained in the storage recessed portion 102b on the left side of FIG. 21A), relatively large force is needed to divide the tablet Th into two because, when the projecting portion 102c which is the exterior surface of the storage recessed portion 102b of the storage body 102 of the press-through pack 101 is pressed with a finger, the two areas R1 and R2 defined by the dividing line Ld on the upper surface Sa of the tablet Th take the same form as the storage recessed portion 102b crushed substantially into a V-shape when seen from side and the finger.

In the case of the tablet Th, since the two areas R1 and R2 defined by the dividing line Ld on the upper surface Sa have concavity, the tablets Th are not face contacted to each other unlike the dividable tablet Tg and hence, twining more rarely occurs in the coating step than the dividable tablet Tg. However, since the two areas R1 and R2 defined by the dividing line Ld on the upper surface Sa of the tablet Th have concavity, when the tablet Th is not divided along the dividing line Ld, such a phenomenon that the tablet Th is divided into two in the vicinity of the dividing line Ld in either one of the two areas R1 and R2 readily occurs (see a crack R11 of FIG. 20B).

Further, when the dividable tablet contained in the press-through pack is divided while it is contained in the press-through pack, since the press-through pack of the prior art is produced based on the condition that the tablets are taken out one by one, the tablets divided into two must be taken out from the storage recessed portions 102 one by one, thereby making it troublesome to take out the divided tablets from the press-through pack.

SUMMARY OF THE INVENTION

The present invention has been made to solve the above problems, and therefore has an object to provide a dividable tablet which can be divided into two easily and accurately without limiting the direction of the upper surface or lower surface of the tablet, is hardly chipped during its production, pneumatically transportation and/or conveyance and eliminates such a problem as twining even when it is coated with a film.

It is another object of the present invention to provide a press-through pack which enables a pharmacist, patient or the like to divide a dividable tablet easily without touching it with his finger and to take out divided tablets at a time easily and simply.

According to a first aspect of the present invention, there is provided a dividable tablet in which a dividing line is formed on the upper surface of the tablet along a center line thereof, ridgelines located on an inner side of the peripheral portion of the tablet and surrounding the dividing line are each formed in two respective areas defined by the dividing line on the upper surface of the tablet, the lower surface of the tablet gradually rises from the peripheral portion of the tablet toward a center portion thereof, and areas around the two ridgelines are each formed by a convex surface.

In this dividable tablet, when a ridgeline is formed in the two areas defined by the dividing line on the upper surface of the tablet, the areas around the two ridgelines are each formed by a convex surface to eliminate a pointed edge portion from the upper surface of the tablet. Therefore, when force is applied to the tablet from above in a vertical direction, the tablet can be divided into two nicely along the dividing line without being chipped. In addition, the tablet is hardly chipped in the tabletting step, during pneumatically transportation and when carried in a press-through pack or a bottle.

Since a pointed edge portion is eliminated from the upper surface of the tablet, core erosion or edge chipping hardly occurs in the coating step.

Since a pointed edge portion is eliminated from the upper surface of the tablet, when the tablet is contained in the storage recessed portion of the press-through pack, there hardly occurs an accident that the sealing sheet is broken by the tablet without being pressed with a finger.

According to a second aspect of the present invention, there is provided a dividable tablet, wherein the two areas defined by the dividing line on the upper surface of the tablet from lines which are the borders of the dividing line to the two ridgelines are each formed by a convex surface.

The "convex surface" of each of the two areas from the lines which are the borders of the dividing line to the two ridgelines is a gently rising surface.

Stated more specifically, the surface of each of the two areas is a gently rising surface as a whole with the curvature thereof increasing continuously from the lines which are the borders of the dividing line toward the ridgelines.

Since the lower surface of this dividable tablet gradually rises from the peripheral portion to the center portion of the tablet, when the upper surface having the dividing line of the tablet contained in the storage recessed portion of the press-through pack faces the sealing sheet, the tablet can be easily divided into two by pressing the protuberant center portion of the lower surface of the tablet with a finger through a projecting portion which is the exterior surface of the storage recessed portion of the storage body of the press-through pack.

Since the areas from the lines which are the borders of the dividing line to the two ridgeline are formed by a convex surface, even when the surface having the dividing line of the tablet contained in the stored recessed portion of the press-through pack faces the storage body, force is applied to the tablet in a direction for opening the dividing line without increasing the strength of the finger because the two areas defined by the dividing line on the upper surface of the tablet have a curved surface corresponding to the shape of the storage recessed portion crushed substantially into a V shape when seen from side and the shape of a finger when the projecting portion which is the exterior surface of the storage recessed portion of the press-through pack is pressed with the finger. Thereby, even when the surface having the dividing line of the tablet contained in the storage recessed portion of the press-through pack faces the storage body, the tablet can be easily divided into two.

Thus, this dividable tablet can be easily divided into two before it is taken out from the press-through pack even when it is contained in the storage recessed portion of the storage body of the press-through pack without limiting the direction of the tablet.

Since the dividable tablet has two convex surfaces on the upper side and one convex surface on the lower side, the tablets are not face contacted to each other but point contacted to each other. Thereby, twining hardly occurs in the coating step.

According to a third aspect of the present invention, there is provided a dividable tablet, wherein the dividing line is formed as a groove deeper than the upper surface of the peripheral portion of the tablet.

The term "deep groove" as used herein means a groove whose deepest portion is located below the peripheral portion of the upper surface of the tablet.

More specifically, the distance in a vertical direction from the apex of the bottom surface of the tablet to the deepest portion of the dividing line is shorter than the distance in a vertical direction from the apex of the bottom surface of the tablet to the upper surface of the peripheral portion of the tablet.

Since the dividing line of this dividable tablet is formed deeper than the dividing line of an ordinary dividable tablet, the tablet can be divided nicely along the dividing line.

According to a fourth aspect of the present invention, there is provided a dividable tablet, wherein the dividing line of the dividable tablet is a V-shaped groove or U-shaped groove.

The term "V-shaped groove" as used herein means a V-shaped groove or a substantially V-shaped groove. The "substantially V-shaped groove" includes, for example, a V-shaped groove having an area around the apex thereof which is formed round or like the apex of a parabola (a curve of secondary degree) or a curved portion near the apex which is formed polygonal with bents.

The term "U-shaped groove" as used herein means a U-shaped groove or a substantially U-shaped groove. The "substantially U-shaped groove" includes, for example, a U-shaped groove having a curved portion that is formed polygonal with bents.

The surface forming the dividing line of the dividable tablet is formed flat or concave and different in shape from the two convex areas from the lines which are the borders of the dividing line to the ridgelines.

Since the dividing line is a V-shaped groove or U-shaped groove, the thickness of the tablet from the deepest portion of the dividing line to the lines which are the borders of the dividing line increases almost uniformly in the case of the V-shaped groove. However, in the case of a U-shaped groove, the thickness of the tablet gradually increases from the deepest portion of the dividing line toward the lines which are the borders of the dividing line within the area of the dividing line and sharply increases in the vicinity of each of the lines which are the borders of the dividing line.

Since the two areas from the lines which are the borders of the dividing line to the ridgelines have a convex surface, the thickness of the tablet sharply increases in the vicinity of each of the lines which are the borders of the dividing line in directions from these lines to the ridgelines.

Thus, changes in the thickness of this dividable tablet within the area of the dividing line are made greatly different from changes in the thickness of the tablet in the vicinity of each of the lines which are the borders of the dividing line in directions from these lines to the ridgelines, the thickness of the tablet is sharply increased in the vicinity of each of the lines which are the borders of the dividing line in directions from these lines to the ridgelines, and force applied to the tablet from the outside per unit volume is made large within the area of the dividing line and made smaller in the vicinity of each of the lines which are the borders of the dividing line in directions from these lines to the ridgelines than force applied to the tablet from the outside per unit volume within the area of the dividing line. Therefore, this tablet can be divided into two nicely along the dividing line.

According to a fifth aspect of the present invention, there is provided a dividable tablet, wherein line portions which are the borders of the dividing line are located at positions above the upper surface of the peripheral portion of the tablet.

The "lines which are the borders of the dividing line" mean two lines which are the borders of the dividing line.

The "positions above the upper surface of the peripheral portion of the tablet" means, more specifically, positions on the two surfaces from the lines which are the borders of the dividing line to the two ridgelines.

When the dividing line is made large (the depth of the dividing line is made large), the dividable tablet can be easily divided into two. However, when the dividing line is formed deep in a vertical direction from the upper surface of the tablet to make the dividing line large (increase the depth of the dividing line), the mechanical strength of the tablet lowers in the area of the dividing line. Therefore, there is such a problem that the tablet may be divided into two of itself even when it is not intended to divide it into two.

The lines which are the borders of the dividing line are not formed on the upper surface of this dividable tablet but formed at positions above the upper surface of the peripheral portion of the tablet. Therefore, the dividing line can be made large (the depth of the dividing line is increased) without forming the dividing line deep in a vertical direction from the upper surface of the tablet.

Thereby, the dividing line can be made large (the depth of the dividing line is increased) without reducing the mechanical strength of the tablet in the area of the dividing line as in the case where the dividing line is formed deep in a vertical direction of the tablet from the upper surface of the tablet. Therefore, there can be obtained a dividable tablet that can be easily divided into two and is not divided into two of itself when it is not intended to divide it into two.

According to a sixth aspect of the present invention, there is provided a dividable tablet, wherein the areas from the two ridgelines on the upper surface of the tablet to the peripheral portion of the tablet are each a steep slope.

The areas from the two ridgelines on the upper side of the tablet to the peripheral portion of the tablet are each formed by a steep slope, and the areas from the lines which are the borders of the dividing line on the upper surface of the tablet to the ridgelines are each formed by a more gently rising surface than the areas from the two ridgelines to the peripheral portion of the tablet. Therefore, when force is applied to the tablet from above in a vertical direction, force is easily applied in a direction for opening the dividing line. Thereby, the tablet can be divided nicely along the dividing line with small force.

According to a seventh aspect of the present invention, there is provided a dividable tablet, wherein the steep slope has a plane or convex surface when it is seen from side.

In this dividable tablet, areas around the two ridgelines formed on the upper surface of the tablet do not have a pointed edge portion but a convex surface. In addition, when force is applied to the tablet from above in a vertical direction, to make it easy to apply force to the tablet in a direction for opening the dividing line, the steep slope of the area from the ridgeline on the upper surface of the tablet to the peripheral portion of the tablet may have a plane or convex surface and not a concave surface when seen from side if the area from the line which is the border of the dividing line on the upper surface of the tablet to the ridgeline can be formed by a gently rising surface.

Therefore, it may be determined from the design of the tablet whether the steep slope of the area from the ridgeline on the upper surface of the tablet to the peripheral portion of the tablet should be formed by a plane or convex surface. Consequently, the shape of the tablet can be determined based on the medical virtue, efficacy and effect of the dividable tablet so that the shape of the tablet can impress doctors, pharmacists, patients and the like.

According to an eighth aspect of the present invention, there is provided a dividable tablet, wherein areas around points of intersection between the dividing line and the peripheral portions of the tablet are chamfered into two convex surfaces sandwiching the dividing line.

In this dividable tablet, since the areas around points of intersection between the dividing line and the peripheral portions of the tablet are chamfered into two convex surfaces sandwiching the dividing line, the tablet is more hardly chipped.

The above dividable tablets of any one of the first to eighth aspects of the present invention may be a bare tablet or coated with a film, sugar or the like.

The above dividable tablets of any one of the first to eighth aspects of the present invention may contain a vehicle, binder and disintegrator and optionally lubricant in addition to effective ingredients. Further, they may be formulated by adding a sweetener, coloring agent, seasonings, antioxidant and the like.

The above dividable tablets can be produced by compression molding methods.

The compression molding methods include one in which mixture powders are tabletted directly and one in which a granulated product having a predetermined particle diameter and particle size distribution is produced from powders by a dry or wet process and formed into granulated powders or fine powders through a drying step and a sizing step, a slight amount of a lubricant is added to the powders, and the mixture is compression molded into a tablet.

Since the above dividable tablets of any one of the first to eighth aspects of the present invention have no pointed portion, sticking, lamination or capping hardly occurs in the tabletting step. Therefore, not only a single eccentric tabletting machine but also a rotary tabletting machine can be used to produce the above dividable tablets by continuous tabletting.

The lubricant may be added to the effective ingredient, the vehicle or the like, and a mixture of the effective ingredient, the vehicle and the lubricant may be tabletted (this tablet production method is called "internal lubricating method"). Alternatively, the lubricant is not added to the effective ingredient, the vehicle or the like but sprayed onto the surface of a punch or die, and a mixture of the effective ingredient, the vehicle and the like may be tabletted using the punch or die having a lubricant layer on the surface (this tablet production method is called "external lubricating method").

Various commonly used coating methods may be used. For example, pan (or drum) coating, flow coating or the like may be used.

The thickness of a coating film is not particularly limited but is preferably in the range of 10 to 50 $\mu$m.

Various vehicles may be used without restriction. Any known vehicles such as saccharides exemplified by lactose, mannitol, saccharose and glucose, starches exemplified by potato starch, corn starch and partly α-ed starch, inorganic salts exemplified by precipitated calcium carbonate, calcium phosphate and sodium chloride, and crystal cellulose may be used.

The vehicle is generally contained in an amount of 10 to 95 parts by weight in one tablet.

Various binders may be used without restriction. Any known binders such as partly saponified polyvinyl alcohol, hydroxypropyl cellulose, hydroxypropyl methyl cellulose, polyvinyl pyrrolidone, pullulan, methyl cellulose, Arabian rubber and starches may be used.

The binder is generally contained in an amount of 0.5 to 5 parts by weight in one tablet.

Various disintegrators may be used without restriction. Any known disintegrators such as crospovidone, hydroxypropyl cellulose having a low degree of substitution, croscarmellose sodium, carboxymethyl cellulose, carboxymethyl cellulose calcium, carboxymethyl starch sodium, partly α-ed starch and hydroxypropyl starch may be used, out of which crospovidone, hydroxypropyl cellulose having a low degree of substitution and croscarmellose sodium are preferred.

The disintegrator is contained in an amount of 1 to 15 parts by weight in one tablet.

Illustrative examples of the lubricant used for tabletting include magnesium stearate, calcium stearate, zinc stearate and stearic acid, talc, hydrogenated vegetable oil and the like, out of which magnesium stearate and calcium stearate are preferred.

The lubricant is generally contained in an amount of 0.01 to 5 parts by weight in one tablet.

According to a ninth aspect of the present invention, there is provided a press-through pack which comprises a storage body having a plurality of storage recessed portions interconnected by plate portions and a sealing sheet having a base and an adhesive layer formed on one side of the base. While the above tablets of any one of the first to eighth aspects of the present invention are each contained in the plurality of storage recessed portions of the storage body, the adhesive layer of the sealing sheet and the plate portions of the storage body are bonded together to seal the storage body with the sealing sheet. The sealing sheet for sealing the storage recessed portions is broken without the rise or peel-off of the adhesive layer of the sealing sheet from the plate portion of the storage body when a projecting portion which is the exterior portion of the storage recessed portion containing the above dividable tablet of any one of the first to eighth aspects of the present invention is pressed with a finger so that the above dividable tablet of any one of the first to eighth aspects of the present invention can be taken out. The sealing sheet is bonded to the plate portions of the storage body so that it can be easily separated from the storage body.

Explaining in more detail the above expression "bonded to the plate portions of the storage body so that it can be easily separated from the storage body", this means that the sealing sheet is bonded such that when part of the sealing sheet of the press-through pack is turned up, it can be easily separated from the plate portion of the storage body without being broken.

In this press-through pack, at least one of the above dividable tablets of the first to eighth aspects of the present invention may be contained in any one of the storage recessed portions of the storage body.

The dividable tablet contained in any one of the storage recessed portions of the storage body may be contained in such a manner that the surface having the dividing line of the dividable tablet contained in the storage recessed portion faces the storage body or the opposite surface faces the storage body. Further, both dividable tablets the surface having the dividing line of which faces the storage body and dividable tablets the opposite surface of which faces the storage body may be each contained in the storage recessed portions of the storage body arbitrarily.

The bonding strength between the sealing sheet and the plate portion of the storage body of this press-through pack is preferably 0.9 N/15 mm in width to 3.1 N/15 mm in width, more preferably 1.9 N/15 mm in width to 2.7 N/15 mm in width when a T peel test is carried out at a peel rate of 200 mm/min.

When a T peel test is carried out at a peel rate of 100 mm/min, the bonding strength is preferably 4.2 N/15 mm in width to 7.0 N/15 mm in width, more preferably 4.8 N/15 mm in width to 6.5 N/15 mm in width.

The unit "N/15 mm in width" as used herein means peel strength when the storage body and the sealing sheet are bonded together, a bonding portion between the storage body and the sealing sheet is cut to a width of 15 mm and a T peel test is made on this cut piece as a test sample.

The term "T peel test" as used herein means a test based on JIS K6845.

Within the above range, when the dividable tablet is taken out by breaking the portion sealing the storage recessed portion of the sealing sheet by pressing the projecting portion which is the exterior surface of the storage recessed portion containing the dividable tablet of the storage body toward the sealing sheet with a finger, the sealing sheet can be separated from the storage body without the rise or peel-off of the adhesive layer of the storage body from the sealing sheet at a bonding portion between the adhesive layer of the sealing sheet and the plate portion of the storage body outside the storage recessed portion (so-called pocket) from which the dividable tablet is taken out of the sealing sheet. Also, when the sealing sheet is peeled and turned up, the sealing sheet can be separated from the storage body without being broken.

In contrast to this, below the above range, though the sealing sheet can be separated from the storage body without being broken when the sealing sheet is peeled and turned up, when the dividable tablet is taken out by breaking the sealing sheet by pressing the projecting portion which is the exterior portion of the storage recessed portion containing the dividable tablet of the storage body toward the sealing sheet with a finger, the sealing sheet peels off or rises from the storage body at the bonding portion between the adhesive layer of the sealing sheet and the plate portion of the storage body outside the storage recessed portion from which the dividable tablet is taken out of the sealing sheet.

Above the above range, when the dividable tablet is taken out by breaking the sealing sheet by pressing the projecting portion which is the exterior portion of the storage recessed portion containing the dividable tablet of the storage body toward the sealing sheet with a finger, the sealing sheet does not peel off or rise from the storage body at the bonding portion between the adhesive layer of the sealing sheet and the plate portion of the storage body outside the storage recessed portion from which the dividable tablet is taken out. However, it is difficult to peel and turn up the sealing sheet and separate it from the storage body. If the sealing sheet is forcedly separated from the storage body, it is partially broken disadvantageously.

The term "adhesive component" as used herein means an adhesive used for heat sealing or cold sealing.

The term "bonding strength reducing component" means a component having the function of reducing the bonding strength of the adhesive component, such as an adhesive having low bonding strength which is generally used as a release agent, filler or the like, as exemplified by a resin used as a release agent or the like, such as a silicone resin or fluororesin. When the storage body is made from polyvinyl chloride, an acrylic resin is used as the bonding strength reducing component.

Illustrative examples of the filler include fine powders of silicon oxide, magnesium silicate, titanium dioxide, zinc oxide, calcium carbonate, alumina, talc and the like.

In this press-through pack, by adding an appropriate amount of a bonding strength reducing component to an adhesive component, the bonding strength of an adhesive is controlled to such a level that the sealing sheet can be separated from the storage body without the peel-off or rise of the sealing sheet from the storage body outside the area of the storage recessed portion (so called "pocket") from which a solid is taken out when the solid is taken out by breaking part of the sealing sheet by pressing the projecting portion which is the exterior surface of the storage recessed portion containing the dividable tablet of the storage body toward the sealing sheet with a finger and that the sealing sheet can be separated from the storage body without being broken when part of the sealing sheet is peeled off from the storage body and turned up.

In the press-through pack of the present invention, the adhesive layer of the sealing sheet may be formed on part of the surface of one side of the sealing sheet.

Various methods are conceivable for partial coating. If the dividable tablets contained in the storage recessed portions of the storage body can be completely sealed, an adhesive may be applied to the surface of a side facing the storage body of the sealing sheet reticulately, linearly or both.

This press-through pack is partially coated with an adhesive to control the bonding strength of the adhesive so that the sealing sheet can be separated from the storage body without the peel-off or rise of the sealing sheet from the storage body outside the so-called pocket when a solid is taken out by breaking part of the sealing sheet by pressing the projecting portion which is the exterior surface of the storage recessed portion containing the dividable tablet with a finger and the sealing sheet can be separated from the storage body without being broken when part of the sealing sheet is peeled off from the storage body and turned up.

Therefore, the dividable tablets contained in this press-through pack can be taken out from the storage recessed portions one by one or at a time by separating the sealing sheet from the storage body.

Further, since the above dividable tablets of any one of the first to eighth aspects of the present invention are each contained in the storage recessed portions of the press-through pack, even when the dividable tablets are contained in the storage recessed portions without limiting the directions of the dividable tablets, the dividable tablets can be each divided into two easily and simply before they are taken out from the storage recessed portions by pressing the projecting portions which are the exterior portions of the storage recessed portions containing the dividable tablets with a finger.

Therefore, before the dividable tablet is taken out from the storage recessed portion, the dividable tablet can be divided into two easily and simply and then the divided tablet can be taken out from the storage recessed portion.

Further, before the dividable tablets contained in the storage recessed portions of the press-through pack are taken out from the storage recessed portions, the dividable tablets can be each divided into two easily and simply and then the divided tablets contained in the press-through pack can be taken out from the storage recessed portions at a time by separating the sealing sheet from the storage body.

BRIEF DESCRIPTION OF THE DRAWINGS

The above and other objects, features and advantages of the present invention will become clear from the following description with reference to the accompanying drawings.

FIGS. 1A to 1C are schematic diagrams of an example of a dividable tablet according to the present invention, wherein FIG. 1A is a plan view, FIG. 1B is a bottom view and FIG. 1C is a side view along line I—I of FIG. 1A.

FIGS. 2A and 2B are side views typically showing a phenomenon which occurs in a dividable tablet according to the present invention when the dividable tablet is divided by applying force from above in a vertical direction, wherein FIG. 2A shows the state of the dividable tablet right before force is applied to the dividable tablet from above in a vertical direction, and FIG. 2B shows the state of the dividable tablet right after force is applied to the dividable tablet from above in a vertical direction.

FIGS. 3A and 3B are side views typically showing a phenomenon which occurs in dividable tablets according to the present invention when the dividable tablets contained in the storage recessed portions of the storage body of a press-through pack are divided by applying force from above in a vertical direction before they are taken out from the storage recessed portions, wherein FIG. 3A is the states of the dividable tablets right before force is applied to the dividable tablets from above in a vertical direction and FIG. 3B shows the states of the dividable tablets right after force is applied to the dividable tablets from above in a vertical direction.

FIGS. 5A to 5C are schematic diagrams of another example of a dividable tablet according to the present invention, wherein FIG. 5A is a plan view, FIG. 5B is a bottom view and FIG. 5C is a side view.

FIGS. 6A to 6C are schematic diagrams of still another example of a dividable tablet according to the present invention, wherein FIG. 6A is a plan view, FIG. 6B is a bottom view and FIG. 6C is a side view.

FIGS. 7A to 7C are schematic diagrams of a further example of a dividable tablet according to the present invention, wherein FIG. 7A is a plan view, FIG. 7B is a bottom view and FIG. 7C is a side view.

FIGS. 12A and 12B are diagrams showing the observation sites of chipping of a tablet in a drop test, wherein FIG. 12A shows the observation sites of the upper surface Sa of the dividable tablet and FIG. 12B shows the observation site of the lower surface Sb of the dividable tablet.

FIGS. 13A to 13C are schematic diagrams of a flat dividable tablet of the prior art, wherein FIG. 13A is a plan view, FIG. 13B is a bottom view and FIG. 13C is a side view along line I—I of FIG. 13A.

FIGS. 14A to 14C are schematic diagrams of a KARATE shape dividable tablet of the prior art disclosed by Japanese Patent Application Laid-open No. Sho 61-289027, wherein FIG. 14A is a plan view, FIG. 14B is a bottom view, and FIG. 14C is a side view along line I—I of FIG. 14A, FIGS. 15A to 15C are schematic diagrams of an example of a dividable tablet disclosed by Japanese Patent Application Laid-open No. Hei 8-53345, wherein

FIGS. 16A to 16C are schematic diagrams of another example of a dividable tablet disclosed by Japanese Patent Application Laid-open No. Hei 8-53345, wherein FIG. 16A is a plan view, FIG. 16B is a bottom view and FIG. 16C is a side view along line I—I of FIG. 16A.

FIGS. 18A and 18B are side views typically showing a phenomenon which occurs in a dividable tablet of the prior art when it is divided by applying force from above in a vertical direction, wherein FIG. 18A shows the state of the dividable tablet right before force is applied to the dividable tablet from above in a vertical direction and FIG. 18B shows the state of the dividable tablet right after force is applied to the dividable tablet from above in a vertical direction.

FIGS. 19A and 19B are diagrams for typically explaining a problem which occurs when dividable tablets of the prior art are each divided into two while they are contained in the storage recessed portions of the storage body of a press-through pack, wherein FIG. 19A shows the states of the dividable tablets right before force is applied to the dividable tablets from above in a vertical direction and FIG. 19B shows the states of the dividable tablets right after force is applied to the dividable tablets from above in a vertical direction.

FIGS. 20A and 20B are diagrams typically showing a phenomenon which occurs in a dividable tablet of the prior art when it is divided by applying force from above in a vertical direction, wherein FIG. 20A shows the state of the dividable tablet right before force is applied to the dividable tablet from above in a vertical direction and FIG. 20B shows the state of the dividable tablet right after force is applied to the dividable tablet from above in a vertical direction.

FIGS. 21A and 21B are diagrams for typically explaining a problem which occurs when dividable tablets of the prior art are each divided into two while they are contained in the storage recessed portions of the storage body of a press-through pack, wherein FIG. 21A shows the states of the dividable tablets right before force is applied to the dividable tablets from above in a vertical direction and FIG. 21B shows the states of the dividable tablets right after force is applied to the dividable tablets from above in a vertical direction.

DETAILED DESCRIPTION OF THE DRAWINGS

With reference to the accompanying drawings, a dividable tablet and a press-through pack according to the present invention will be described in more detail.

Figure 1A:
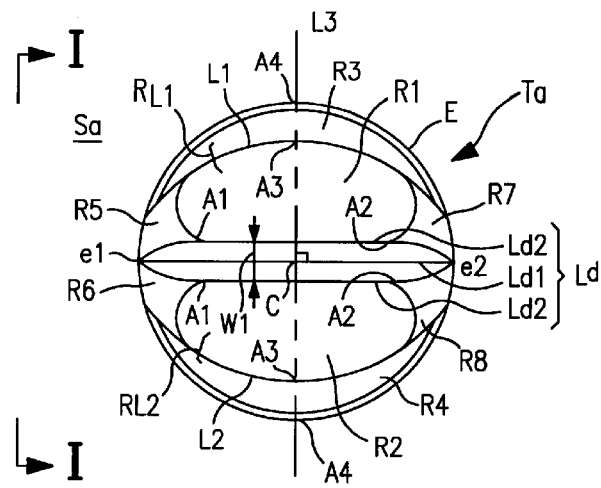
Figure 1B:
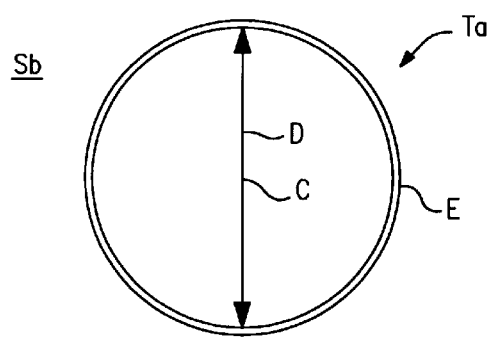
Figure 1C:
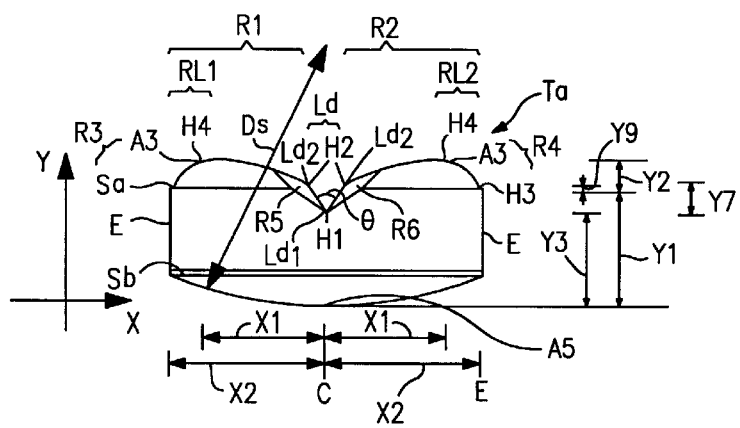

FIGS. 1A to 1C are schematic diagrams of an example of the dividable tablet according to the present invention. FIG. 1A is a plan view, FIG. 1B is a bottom view and FIG. 1C is a side view.

This dividable tablet Ta has a round shape when seen from above as shown in FIG. 1A and a dividing line Ld is formed on an upper surface Sa of the dividable tablet along a center line.

Two areas R1 and R2 defined by the dividing line Ld on the upper surface Sa of the dividable tablet Ta are symmetrical about the dividing line Ld.

The dividing line Ld is a deep groove extending from one peripheral portion e1 of the tablet Ta to the other peripheral portion e2 on the opposite side.

Describing in more detail, in this tablet Ta, as shown in FIGS. 1A and 1C, the dividing line Ld is a V-shaped groove.

When the dividing ease of the dividing line Ld is taken into consideration, the apex angle θ of the V-shaped groove constituting the dividing line Ld is preferably in the range of 40° to 90°, more preferably 45° to 90°, the most preferably 50° to 60°.

A position H2 in a vertical direction (direction of the Y axis shown in FIG. 1C) of a line Ld2 which is the border of the dividing line Ld may be any position if it is higher than a position H1 in a vertical direction (direction of the Y axis shown in FIG. 1C) of the deepest portion Ld1 (line formed at the deepest portion of the dividing line) of the dividing line Ld.

However, when the ease of dividing the tablet Ta is taken into consideration, the position H2 is preferably higher than a position H3 in a vertical direction of the peripheral portion E of the upper surface Sa.

The position H1 in a vertical direction of the deepest portion Ld1 of the dividing line Ld may be located above the position H3 of the peripheral portion E of the upper surface Sa of the tablet Ta but preferably located below the position H3 of the peripheral portion E of the upper surface Sa of the tablet Ta when the ease of dividing the tablet Ta and the like are taken into consideration.

Stated more specifically, the distance Y3 in a vertical direction from the apex (apex A5 shown in FIG. 1C) of the bottom of the tablet Ta to the deepest portion Ld1 of the dividing line Ld is preferably shorter than the distance Y1 in a vertical direction from the apex A5 of the bottom of the tablet Ta to the upper surface Sa of the peripheral portion E of the tablet Ta.

Although the dividable tablet Ta is easily divided into two if the dividing line Ld is made Large (the deepest portion Ld1 of the dividing line Ld is made deep), when the deepest portion Ld1 of the dividing line Ld is formed deep in a vertical direction (direction of the Y axis shown in FIG. 1C) from the position H3 of the upper surface Sa of the tablet Ta toward the lower surface Sb of the tablet Ta, the mechanical strength of the tablet Ta weakens and the tablet Ta is easily divided into two of itself when it does not need to be divided.

To solve this problem, it is preferred to enlarge the dividing line Ld by making the position of the deepest portion Ld1 of the dividing line Ld not so deeper than the position H3 of the upper surface Sa of the tablet Ta and the positions A2 and A2 of the lines Ld2 and Ld2 which are the borders of the dividing line Ld higher than the position H3 of the upper surface Sa of the tablet Ta.

Ridgelines L1 and L2 are formed in the two areas R1 and R2 defined by the dividing line Ld on the upper surface Sa of the tablet Ta in such a manner that they are located on the inner side of the peripheral portion E of the tablet Ta to surround the dividing line Ld, respectively.

Areas RL1 and RL2 around the ridgelines L1 and L2 are each formed by a convex surface to eliminate a pointed edge portion.

The ridgeline L1 formed in the area R1 of the areas R1 and R2 is formed by a gently rising surface (convex surface) rising from the line Ld2 which is the border of the dividing line Ld and a convex surface formed by a steep slope R3 on the upper surface Sa of the tablet Ta along the peripheral portion E of the tablet Ta on the peripheral portion E side of the tablet Ta, and the area RL1 around the ridgeline L1 is formed by a convex surface.

Describing in more detail the gently rising surface (convex surface) formed from the line Ld2 which is the border of the dividing line Ld in the area R1, the surface of the area R1 is a gently rising surface as a whole with the curvature thereof increasing continuously from the line Ld2 which is the border of the dividing line Ld toward the ridgeline L1.

The steep slope R3 and the rising surface in the area R1 or R2 are connected to each other at the top of the ridgeline L1 or in the vicinity of the top of the ridgeline L1. The steep slope R3 and the rising surface in the area R1 or R2 may be connected to each other by a plurality of curved surfaces.

The ridgeline L2 formed in the area R2 of the two areas R1 and R2 is also formed by a gently rising surface (convex surface) rising from the line Ld2 which is the border of the dividing line Ld and a convex surface formed by a steep slope R4 on the upper surface Sa of the tablet Ta along the peripheral portion E of the tablet Ta on the peripheral portion E side of the tablet Ta, and the area RL2 around the ridgeline L2 is also formed by a convex surface.

Describing in more detail the gently rising surface (convex surface) formed from the line Ld2 which is the border of the dividing line Ld in the area R2, the surface of the area R2 is a gently rising surface as a whole with the curvature thereof increasing continuously from the line Ld2 which is the border of the dividing line Ld toward the ridgeline L2.

As required, an area around the point of intersection between the dividing line Ld and the ridgeline L1 and an area around the point of intersection between the dividing line Ld and the ridgeline L2 may be chamfered.

Areas R5 and R6 near one peripheral portion e1 where the dividing line Ld intersects the peripheral portion E of the tablet Ta and areas R7 and R8 near the other peripheral portion e2 where the dividing line Ld intersects the peripheral portion E of the tablet Ta are chamfered into a convex surface.

They may be chamfered into a plane surface.

The ridgeline L1 extends to a point of intersection A1 between the line Ld2 which is the border of the dividing line Ld and the chamfered area R5 and to a point of intersection A2 between the line Ld2 which is the border of the dividing line Ld and the chamfered area R7, gradually rises from the points of intersection A1 and A2 in a vertical direction (direction of the Y axis) and reaches the highest position H4 in a vertical direction (direction of the Y axis) at a point of intersection A3 between the center point C of the tablet Ta and a line L3 crossing the dividing line Ld.

The ridgeline L2 also extends to the point of intersection A1 between the line Ld2 which is the border of the dividing line Ld and the chamfered area R6 and the point of intersection A2 between the line Ld2 which is the border of the dividing line Ld and the chamfered area R8, gradually rises from the points of intersection A1 and A2 in a vertical direction (direction of the Y axis) and reaches the highest position H4 in a vertical direction (direction of the Y axis) at the point of intersection A3 between the center point C of the tablet Ta and the line L3 crossing the dividing line Ld.

The lower surface Sb of the tablet Ta has such a form that it gradually rises from the peripheral portion E of the tablet Ta toward the center portion C, that is, convexity (see FIG. 1C).

When the distance in a horizontal direction (direction of the X axis shown in FIG. 1C) from the center point C of the tablet Ta to the point of intersection A2 between the line L3 crossing the dividing line Ld and passing the center point C and the ridgeline L1 is represented by X1 and the distance in a horizontal direction (direction of the X axis shown in FIG. 1C) from the center point C of the tablet Ta to the point of intersection A4 between the line L3 crossing the dividing line Ld and passing the center point C and the peripheral portion E is represented by X2, the ratio of the distance X1 to the distance X2 (($X1/X2$)×100) is preferably in the range of 60 to 80%, more preferably 70 to 80%, particularly preferably 75%.

When the distance in a vertical direction from the center point C of the tablet Ta to the upper surface Sa of the peripheral portion E of the tablet Ta is represented by Y1 and the distance in a vertical direction from the upper surface Sa of the peripheral portion E of the tablet Ta to the point of intersection A3 between the line L3 crossing the dividing line Ld and passing the center point C and the ridgeline L1 is represented by Y2, the ratio of the distance Y1 to the distance Y2 (($Y1/Y2$)×100) is preferably in the range of 20 to 50%, more preferably 20 to 30%, particularly preferably 23 to 25%.

As for the curvature of a curve formed on the lower surface Sb of the tablet Ta and gradually rising from the peripheral portion E to the center portion C of the tablet Ta, that is, convexity, the ratio of the radius of the curve (the radius Ds of the curve shown in FIG. 1C) to the diameter of the tablet Ta (the diameter D of the tablet Ta shown in FIG. 1B) is preferably in the range of 1.25 to 2.5.

The diameter D of the tablet Ta is preferably in the range of 5 to 14 mm, more preferably 7 to 10 mm when patient compliance and ease of division for administration without dividing it is taken into consideration.

A pharmacist, patient or the like can divide this dividable tablet Ta along the dividing line Ld by directly grasping the two areas R1 and R2 with his fingers when the tablet is to be divided.

Further, there is such an advantage that the tablet Ta can be divided into two by pressing it down from above.

Figure 2A:
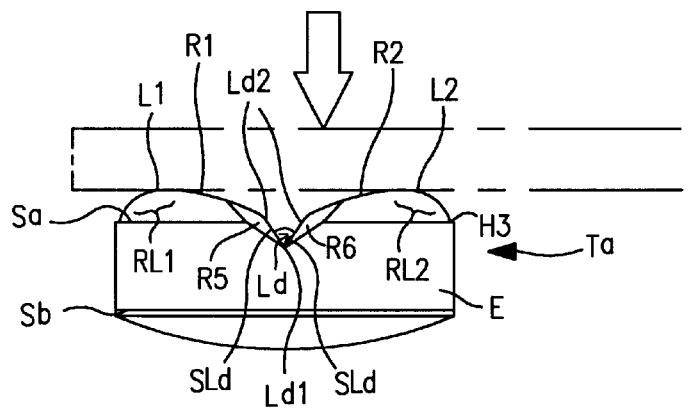
Figure 2B:
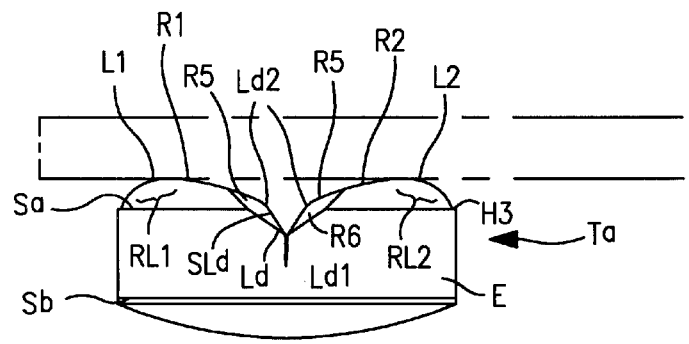

FIGS. 2A and 2B are side views typically showing a phenomenon which occurs in the dividable tablet Ta when force is applied to the dividable tablet Ta from above in a vertical direction. FIG. 2A shows the state of the dividable tablet Ta right before force is applied to the dividable tablet Ta from above in a vertical direction and FIG. 2B shows the state of the dividable tablet Ta right after force is applied to the dividable tablet Ta from above in a vertical direction.

In the dividable tablet Ta, the areas RL1 and RL2 around the ridgelines L1 and L2 on the upper surface Sa of the tablet Ta are each formed by a convex surface (see FIG. 2A) so that a pointed edge portion Pe which is seen on the upper surfaces Sa of the tablets Tg and Th is eliminated. Therefore, the areas RL1 and RL2 around the ridgelines are not crushed or chipped. Thereby, the tablet Ta can be divided into two nicely by pressing it down from above.

Since a pointed edge portion Pe which is seen in the tablets Tg and Th is eliminated from the upper surface Sa of the dividable tablet Ta, capping hardly occurs in the tabletting step (see FIG. 2B).

Since a pointed edge portion Pe is eliminated from the upper surface Sa of the tablet Ta, even when the tablets Ta collide with each other, core erosion, edge chipping or the like hardly occurs in the coating step.

When the tablets Ta are pneumatically transported from one place to another, even if they collide with each other or with a transport pipe, they are hardly chipped because they have no pointed edge portion Pe.

Since the dividable tablet Ta has two projecting surfaces R1 and R2 on the upper side and a convex surface R6 on the lower side, the tablets are not face contacted to each other but point contacted to each other. Thereby, twinning hardly occurs in the coating step.

Further, in this tablet Ta, the dividing line is a V-shaped groove.

When the dividing line Ld is a V-shaped groove, two inclined surfaces SLd and SLd forming the V-shaped groove and connecting the lines Ld2 and Ld2 which are the borders of the dividing line Ld and the deepest portion Ld1 are flat.

The two areas R1 and R2 from the lines Ld2 and Ld2 which are the borders of the dividing line Ld to the ridge-lines L1 and L2 have convexity in this tablet Ta and are made different in shape from the two inclined surfaces SLd and SLd forming the V-shaped groove.

As a result, as the dividing line Ld is a V-shaped groove, the increasing rate of the thickness (thickness in a vertical direction (direction of the Y axis shown in FIG. 1C)) of the tablet Ta from the deepest portion Ld1 of the dividing line Ld to the lines Ld2 and Ld2 which are the borders of the dividing line Ld with respect to a horizontal direction (direction of the X axis shown in FIG. 1C) is constant. The thickness increases uniformly.

Since the two areas R1 and R2 from the lines Ld2 and Ld2 which are the borders of the dividing line Ld to the ridge-lines L1 and L2 have a convex surface, in the vicinity of each of the lines Ld2 and Ld2 which are the borders of the dividing line Ld in directions from the lines Ld2 and Ld2 to the ridgelines L1 and L2, the thickness (thickness in a vertical direction (direction of the Y axis shown in FIG. 1C) of the tablet Ta from the deepest portion Ld1 of the dividing line Ld to the lines Ld2 and Ld2 which are the borders of the dividing line Ld with respect to a horizontal direction (direction of the X axis shown in FIG. 1C) sharply increases.

Thus, changes in the thickness in a vertical direction with respect to a horizontal direction of the tablet Ta within the area of the dividing line Ld are made greatly different from changes in the thickness in a vertical direction with respect to a horizontal direction of the tablet Ta in the vicinity of each of the lines Ld2 and Ld2 which are the borders of the dividing line Ld in directions from the lines Ld2 and Ld2 to the ridgelines L1 and L2, the thickness in a vertical direction with respect to a horizontal direction of the tablet Ta in the vicinity of each of the lines Ld2 and Ld2 which are the borders of the dividing line Ld in directions from the lines Ld2 and Ld2 to the ridgelines L1 and L2 is sharply increased, and force applied to the tablet Ta from the outside per unit volume is made large within the area of the dividing line Ld and smaller in the vicinity of each of the lines Ld2 and Ld2 which are the borders of the dividing line Ld in directions from the lines Ld2 and Ld2 to the ridgelines L1 and L2 than force applied to the tablet Ta from the outside per unit volume within the area of the dividing line Ld. Therefore, when the tablet Ta is divided into two, it can be divided along the dividing line Ld nicely.

Further, in this tablet Ta, the position H1 of the deepest portion Ld1 of the dividing line Ld is located below the position H3 of the upper surface of the peripheral portion E of the tablet Ta and the dividing line Ld is formed deeper than the dividing line of an ordinary dividable tablet. Therefore, the tablet Ta can be divided along the dividing line nicely.

Further, when this tablet Ta is wrapped in a press-through pack and contained in the storage recessed portion of the storage body of the press-through pack without limiting the direction of the tablet, it can be divided into two before it is taken out from the press-through pack.

This will be described in more detail with reference to FIGS. 3A and 3B.

Figure 3A:
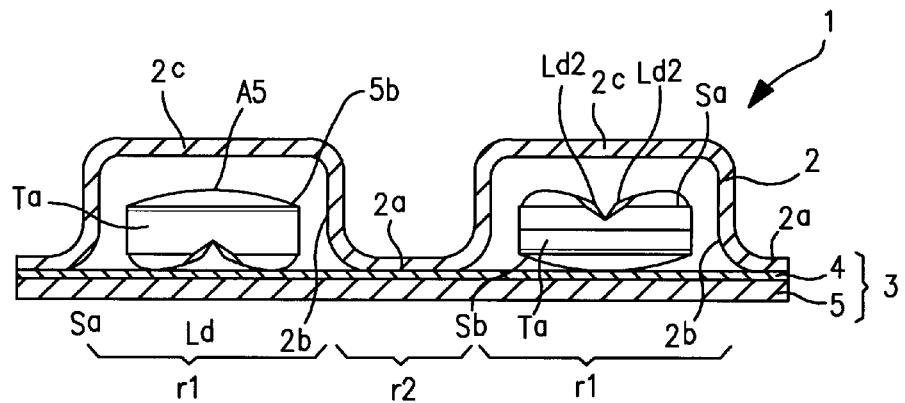
Figure 3B:
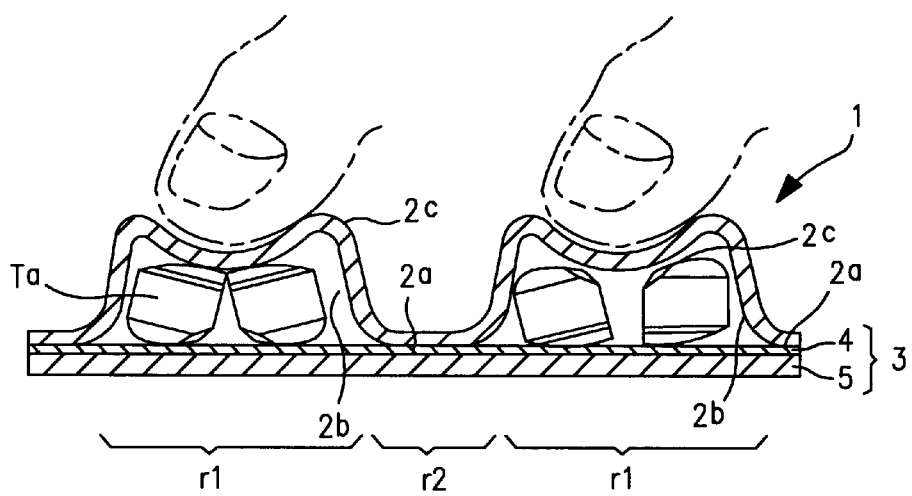
Figure 4A:
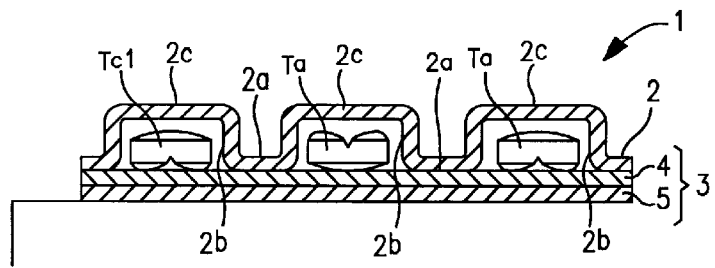
FIGS. 4A to 4D are diagrams typically showing examples of use of a press-through pack according to the present invention.
Figure 4B:
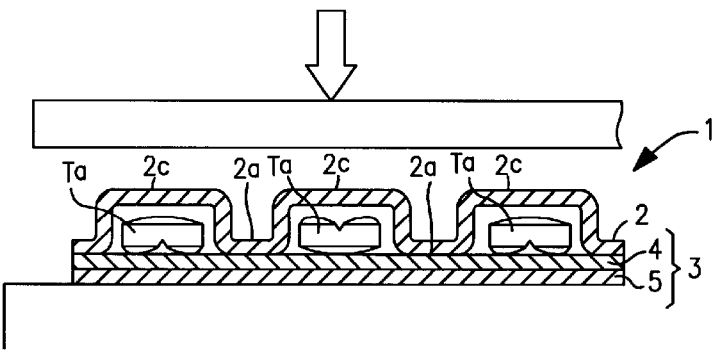
Figure 4C:
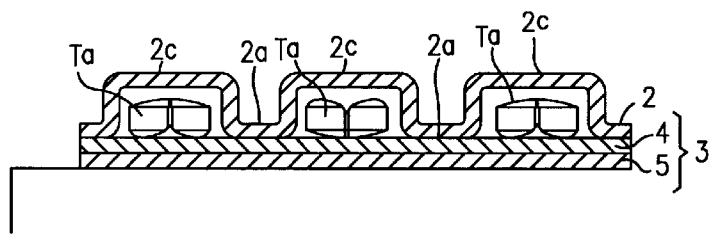
Figure 4D:
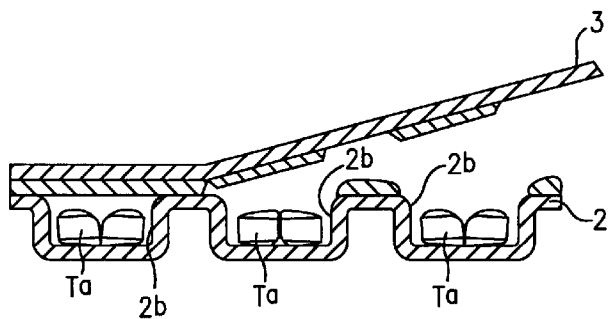

FIGS. 3A and 3B are side views typically showing a phenomenon which occurs in the dividable tablets Ta when the dividable tablets Ta contained in the storage recessed portions 2b of the storage body 2 of a press-through pack 1 are divided by applying force from above in a vertical direction before they are taken out from the storage recessed portions 2b. FIG. 3A shows the state of the dividable tablets Ta right before force is applied to the dividable tablets Ta from above in a vertical direction and FIG. 3B shows the state of the dividable tablets Ta right after force is applied to the dividable tablets Ta from above in a vertical direction.

Since the lower surface Sb of the tablet Ta gradually rises from the peripheral portion E of the tablet Ta toward the center portion C, when the upper surface Sa on the side having the dividing line Ld of the tablet contained in the storage recessed portion 2b of the storage body 2 of the press-through pack 1 faces a sealing sheet 3 (see the tablet Ta contained in the storage recessed portion 2b on the left side of FIG. 3A), the tablet Ta can be easily divided into two by pressing the protuberant center portion A5 of the lower surface Sb of the tablet Ta with a finger through a projecting portion 2c which is the exterior portion of the storage recessed portion 2b of the storage body 2 of the press-through pack 1 (see the tablet Ta contained in the storage recessed portion 2b on the left side of FIG. 3B).

Since the areas from the lines Ld2 and Ld2 which are the borders of the dividing line Ld to the two ridgelines L1 and L2 are each formed by a convex surface, even when the side having the dividing line Ld of the tablet Ta contained in the storage recessed portion 2b of the press-through pack 1 faces the storage body 2 (seethe tablet Ta contained in the storage recessed portion 2b on the right side of FIG. 3A), the force of the finger is easily transmitted to the tablet Ta because the two areas R1 and R2 defined by the dividing line Ld on the upper surface Sa of the tablet Ta have a convex surface corresponding to the shape of the storage recessed portion 2b crushed substantially into a V-shape when seen from side and the shape of a finger when the projecting portion 2c which is the exterior portion of the storage recessed portion 2b of the press-through pack 1 is pressed with the finger. Thereby, force is applied to the tablet in a direction for opening the dividing line Ld without increasing the strength of the finger so that the tablet Ta can be easily divided into two even when the side having the dividing line Ld of the tablet Ta contained in the storage recessed portion 2b of the press-through pack 1 faces the storage body 2 (see the tablet Ta contained in the storage recessed portion 2b on the right side of FIG. 3B).

The press-through pack shown in FIGS. 3A and 3B comprises the storage body 2 and the sealing sheet 5 and is structured such that the adhesive layer 4 of the sealing sheet 3 is bonded to the plate portions 2a, . . . , 2a of the storage body 2.

The storage body 2 is thermally molded according to the shape of the dividable tablets Ta, . . . , Ta to be contained therein, and a plurality of storage recessed portions 2b, . . . , 2b are interconnected by a plurality of plate portions 2a, . . . , 2a.

The material of the storage body 2 is a generally used thermoplastic synthetic resin, such as polyvinyl chloride, polypropylene, polystyrene or cyclic polyolefin. When the above materials for the storage body are used, the plurality of storage recessed portions 2b, . . . , 2b can be easily formed by thermal molding according to the shape of the dividable tablets Ta, . . . , Ta to be contained therein.

The sealing sheet 3 has a base 5 and an adhesive layer 4 formed on one side of the base 5.

Various kinds of materials which are used as packing materials may be used if they can seal hermetically the dividable tablets Ta, . . . , Ta contained in the storage recessed portions 2b, . . . , 2b of the storage body 2 and can be easily broken by the dividable tablets Ta, . . . , Ta contained in the storage recessed portions 2b, . . . , 2b by pressing the projecting portions 2c, . . . , 2c which are the exterior surfaces of the storage recessed portions 2b, . . . , 2b of the storage body 2 in the direction of the sealing sheet 3. Preferred examples of the materials include aluminum foil, glassine paper, synthetic resin sheets which contain a filler for making the sheet breakable, paper and the like.

Stated more specifically, when aluminum foil is used as the base 5 of the sealing sheet 3, hard foil preferably having a thickness of 5 to 30 $\mu$m, more preferably 15 to 25 $\mu$m, is used.

When glassine paper is used as the base 5 of the sealing sheet 3, it preferably has a basis weight (weight per m$^2$) of 30.5 g/m$^2$.

When a synthetic resin sheet which contains a filler for making the sheet breakable is used as the base 5 of the sealing sheet 3, it preferably has a thickness of 9 to 100 $\mu$m, more preferably 12 to 80 $\mu$m.

The synthetic resin is preferably a thermoplastic synthetic resin such as polyvinyl chloride, polypropylene, polystyrene, linear polyolefin or the like.

Illustrative examples of the filler to be contained in the synthetic resin include silicon oxide, magnesium silicate, titanium dioxide, zinc oxide, calcium carbonate, alumina, talc and the like and a filler having an average particle diameter of 1 to 10 $\mu$m is mixed with a synthetic resin in an amount of 5 to 15 wt %, preferably 5 to 70 wt %.

When paper is used as the base 5 of the sealing sheet 3, paper having a basis weight of 13 to 100 g/m$^2$ is preferably used.

As for the physical properties and composition of the base 5 of the sealing sheet 3 described above, the base 5 of the sealing sheet 3 should have such toughness that the dividable tablet Ta can be taken out by breaking portions r1, . . . , r1 sealing the storage recessed portions 2b, . . . , 2b of the sealing sheet 5 sealing the storage recessed portion 2b when mainly the projecting portion 2c which is the exterior surface of the storage recessed portion 2b containing the dividable tablet Ta of the storage body 2 is pressed with a finger in the direction of the sealing sheet 5.

The above constitution is the same as that of the press-through pack 101 of the prior art. However, in this press-through pack 1, the bonding strength between the adhesive layer 4 of the sealing sheet 3 and the plate portions 2a, . . . , 2a of the storage body 2 is controlled such that only the portions r1, . . . , r1 (so-called pocket portions) of the sealing sheet 3 sealing the storage recessed portions 2b, . . . , 2b are broken without spreading the break of the sealing sheet 3 to bonding portions r2, . . . , r2 between the plate portions 2a and the adhesive layer 4 and the dividable tablets Ta, . . . , Ta can be taken out one by one when the projecting portions 2c, . . . , 2c which are exterior surfaces of the storage recessed portions 2b, . . . , 2b containing the dividable tablets Ta, . . . , Ta are each pressed with a finger in the direction of the sealing sheet 3 and that the sealing sheet 3 can be easily separated from the storage body 2 without being broken halfway when it is peeled and turned up.

As for how to adjust the bonding strength of the sealing sheet 3, the case where the bonding strength is controlled by the components of an adhesive forming the adhesive layer 4 and the case where the bonding strength of the adhesive is controlled by a method for coating on the base 5 of the sealing sheet 3 will be described hereinunder.

A. The Case where Bonding Strength is Controlled by the Components of the Adhesive When the bonding strength is controlled by components forming the adhesive, an appropriate amount of a bonding strength reducing component is blended with an adhesive component.

Stated more specifically, any component may be used as the adhesive component if it can bond the storage body 2 to the base 5 of the sealing sheet 3. A thermoplastic resin which allows for heat sealing or a cold sealing adhesive which allows for cold sealing may be used.

The thermoplastic resin which allows for heat sealing is not limited to the following substances. When the storage body 2 is made from polyvinyl chloride, for example, a vinyl chloride-vinyl acetate copolymer is preferred. When the storage body 2 is made from polypropylene, for example, chlorinated polypropylene or carboxylated polypropylene is preferred. When the storage body 2 is made from polystyrene, for example, a mixture of a vinyl chloride-vinyl acetate copolymer and an acrylic resin is preferred.

Illustrative examples of the cold sealing adhesive include acrylic resins, silicon resins, rubber and the like.

The "cold sealing adhesive" refers to an adhesive which can bond a member to another member by pressure when these members are to be bonded together.

Any substance can be used as the bonding strength reducing component to be blended with the adhesive if it can reduce bonding strength between the adhesive layer 4 of the sealing sheet 3 and the storage body 2 or bonding strength between the adhesive layer 4 of the sealing sheet 3 and the base 5 of the sealing sheet 3.

Preferred examples of the substance include resins which are used as a release agent, such as silicone resin and fluororesin, acrylic resins and linear polyester resins and the like.

Fine powders which are used as a filler, such as silicon oxide, magnesium silicate, titanium dioxide, zinc oxide, calcium carbonate, alumina and talc, are also preferred as the above substance.

The ratio of the adhesive component to the bonding strength reducing component in the adhesive is determined by a bonding strength test, extrusion test and peel test which will be described hereinafter.

B. The Case where Bonding Strength is Controlled by a Method for Coating the Adhesive to the Base of the Sealing Sheet In this case, desired bonding strength can be obtained by coating the adhesive on all or part of the base 5 of the sealing sheet 3 or by controlling the amount of coating per unit area of the adhesive to be applied to the base 5 of the sealing sheet 3.

Partial coating may be carried out as follows. The adhesive may be coated reticulately, linearly or both on the surface facing the storage body 2 of the sealing sheet if the dividable tablets Ta, . . . , Ta contained in the storage recessed portions 2b of the storage body can be completely sealed hermetically.

To control the amount of coating per unit area of the adhesive to be coated on the base 5 of the sealing sheet 3, an adhesive containing an appropriate amount of a diluent is used or the thickness of a coating film per unit area of the adhesive to be coated on the base 5 of the sealing sheet 3 may be adjusted.

When the bonding strength is controlled by a method for coating the adhesive on the base 5 of the sealing sheet 3, it should be noted that the bonding strength reducing component may or may not be contained in the adhesive.

In this press-through pack 1, the dividable tablets Ta, . . . , Ta are each contained in the storage recessed portions 2b, . . . , 2b.

Therefore, the dividable tablets Ta, . . . , Ta can be taken out from the storage recessed portions 2b, . . . , 2b individually by pressing the projecting portions 2c, . . . , 2c which are the exterior surfaces of the storage recessed portions 2b, . . . , 2b with a finger or the like.

A pharmacist, patient or the like can take out a required number of dividable tablets Ta, . . . , Ta from the storage recessed portions 2b, . . . , 2b individually and then divide each of them into two along the dividing line Ld easily by grasping the tablet Ta with his finger or the like if necessary.

Since the dividable tablets Ta, . . . , Ta whose directions are not limited are contained in the storage recessed portions 2b, . . . , 2b in this press-through pack 1 when divided into two, they can be each divided into two while they are contained in the storage recessed portions 2b, . . . , 2b by bringing the sealing sheet 3 into contact with a flat surface such as a table and pressing the projecting portions 2c, . . . , 2c which are the exterior surfaces of the storage recessed portions 2b, . . . , 2b before they are taken out from the storage recessed portions 2b, . . . , 2b.

Therefore, after a required number of dividable tablets Ta out of the dividable tablets Ta, . . . , Ta are each divided into two while they are contained in the storage recessed portions 2b, the divided dividable tablets Ta, . . . , Ta can be taken out from the storage recessed portions 2b by pressing the projecting portions 2c which are the exterior surfaces of the storage recessed portions 2b containing the divided dividable tablets Ta with a finger or the like.

Further, in this press-through pack 1, when the sealing sheet 3 is peeled and turned up, the sealing sheet 3 can be easily separated from the storage body 2 without being broken halfway. Therefore, when the sealing sheet 3 is peeled off from the storage body 2 and turned up, all the dividable tablets Ta, . . . , Ta contained in the press-through pack 1 can be taken out from the press-through pack 1 at a time.

Moreover, since the dividable tablets Ta, . . . , Ta whose directions are not limited are contained in the press-through pack 1 when divided into two, as shown in FIGS. 4A to 4D, all the dividable tablets Ta, . . . , Ta can be each divided into two (FIGS. 4A to FIG. 4C) by bringing the sealing sheet 3 into contact with a flat surface such as a table and pressing the projecting portions 2c, . . . , 2c which are the exterior surfaces of the storage recessed portions 2b, . . . , 2b with a finger, jig or the like before they are taken out from the storage recessed portions 2b, . . . , 2b and then all the dividable tablets Ta, . . . , Ta which are divided into two and contained in the press-through pack 1 can be taken out from the press-through pack 1 at a time by peeling off the sealing sheet 3 from the storage body 2 and turning it up.

Thereby, the dividable tablets can be divided into two before they are taken out from the storage recessed portions 2b of the storage body 2 by using this press-through pack 1. Therefore, the tablet Ta cannot be contaminated by bacteria, mold or the like adhered to a finger when it is divided into two with the finger or the like. In addition, when a large number of tablets are prepared at a hospital or the like, all the dividable tablets Ta, . . . , Ta contained in the press-through pack 1 can be taken out from the press-through pack at a time by peeling off the sealing sheet 3 from the storage body 2 and turning it up.

Further, when a large number of the tablets Ta, . . . , Ta which are divided into two must be prepared, use of this press-through pack 1 makes it possible to divide all the dividable tablets Ta, . . . , Ta into two before they are taken out from the storage recessed portions 2b, . . . , 2b and then take out all the dividable tablets Ta, . . . , Ta which are divided into two from the press-through pack 1 at a time by peeling off the sealing sheet 3 from the storage body 2 and turning it up. Therefore, the preparation work of the tablets at a hospital or the like can be greatly improved.

The above dividable tablet Ta has been described as a preferred embodiment of the present invention to illustrate the present invention. The present invention is not limited to this dividable tablet Ta.

FIGS. 5A to 5C, FIGS. 6A to 6C to FIGS. 7A to 7C are diagrams showing modifications of the present invention.

Figure 5A:
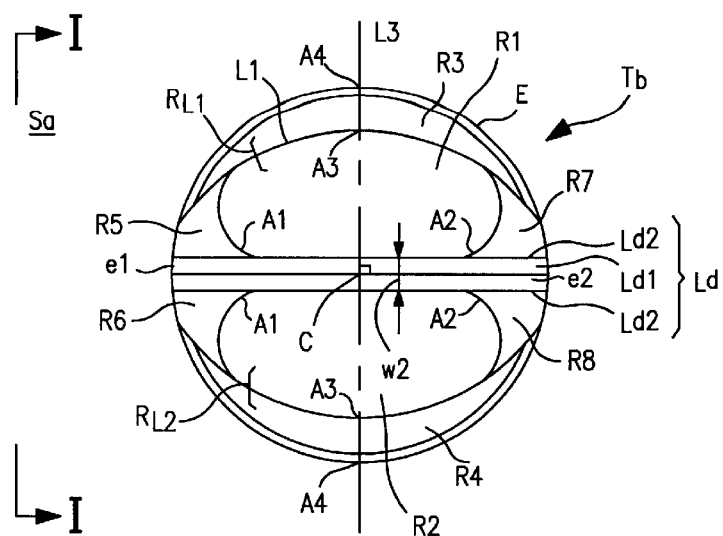
Figure 5B:
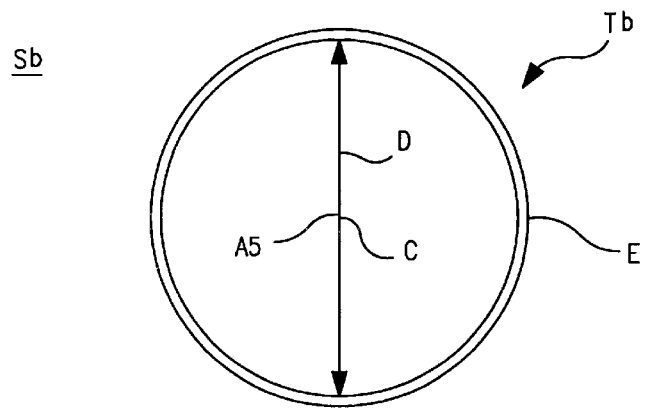
Figure 5C:
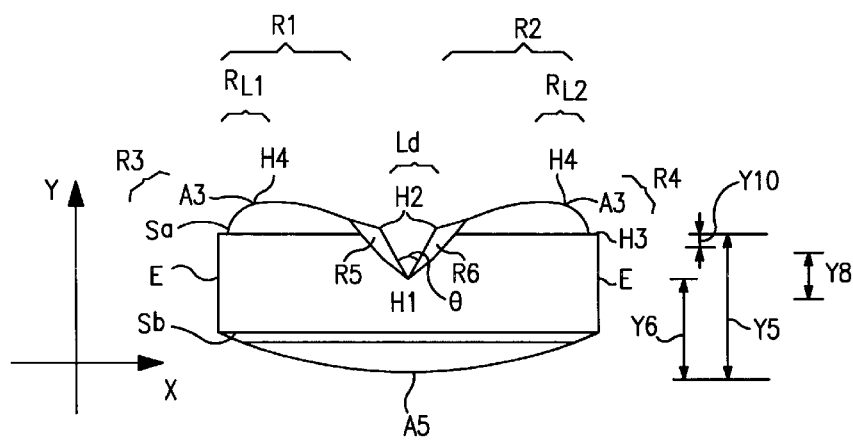

FIGS. 5A to 5C are schematic diagrams of another example of a dividable tablet according to the present invention. FIG. 5A is a plan view, FIG. 5B is a bottom view and FIG. 5C is a side view.

This dividable tablet Tb differs from the dividable tablet Ta in that the dividing line Ld is larger than that of the dividable tablet Ta.

That is, the width between lines Ld2 and Ld2 which are the two borders of the dividing line Ld of this dividable tablet Tb (width w2 shown in FIG. 5A) is larger than the width between lines Ld2 and Ld2 which are the two borders of the dividing line Ld of the dividable tablet Ta (w1 shown in FIG. 1A) (w2>w1). Further, the distance in a vertical direction from the lines Ld2 and Ld2 which are the two borders of the dividing line Ld of the dividable tablet Tb to the deepest portion Ld1 (distance Y8 shown in FIG. 5C) is longer than the distance in a vertical direction from the lines Ld2 and Ld2 which are the two borders of the dividing line Ld of the dividable tablet Ta to the deepest portion Ld1 (distance Y7 shown in FIG. 1C) (Y8>Y7).

Since the size of the dividing line Ld of the dividable tablet Tb is thereby larger than that of the dividable tablet Ta, the dividable tablet Tb can be easily divided into two with smaller force than that of the dividable tablet Ta.

Moreover, to increase the size of the dividing line Ld in this dividable tablet Tb, the distance in a vertical direction from the position H3 of the upper surface Sa of the peripheral portion E of the tablet Tb to the lines Ld2 and Ld2 which are the borders of the dividing line Ld (distance Y10 shown in FIG. 5C) is made longer than the distance in a vertical direction from the position H3 of the upper surface Sa of the peripheral portion E of the tablet Ta to the lines Ld2 and Ld2 which are the borders of the dividing line Ld (distance Y9 shown in FIG. 1C) (Y10>Y9), and the distance in a vertical direction from the deepest portion Ld1 of the dividing line Ld to the apex A5 of the bottom portion of the tablet Tb (distance Y6 shown in FIG. 5C) is made equal to the distance in a vertical direction from the deepest portion Ld1 of the dividing line Ld of the tablet Ta to the apex A5 of the bottom portion of the tablet Ta (Y3 shown in FIG. 1C) (Y6=Y3). Therefore, the mechanical strength of the tablet Tb at the deepest portion Ld1 of the dividing line Ld is substantially the same as the mechanical strength of the tablet Ta at the deepest portion Ld1 of the dividing line Ld. Thereby, when the dividable tablet Tb is divided into two, which is technically reciprocal, it can be divided into two with small force because the size of the dividing line Ld is large.

Since the other portions of this dividable tablet Tb are the same as those of the dividable tablet Ta in shape, corresponding portions are given the same reference symbols and their descriptions are omitted.

Figure 6A:
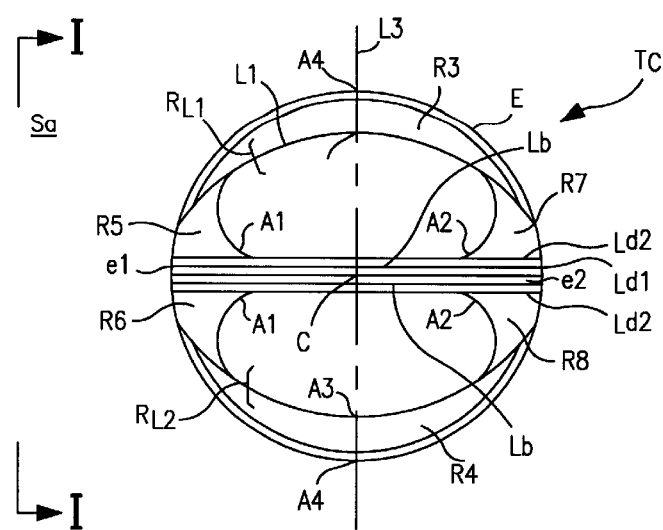
Figure 6B:
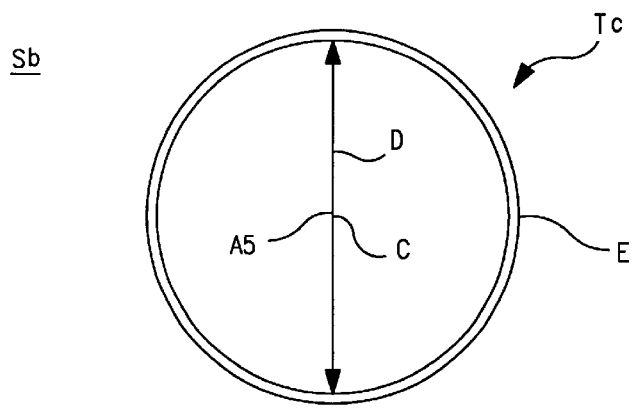
Figure 6C:
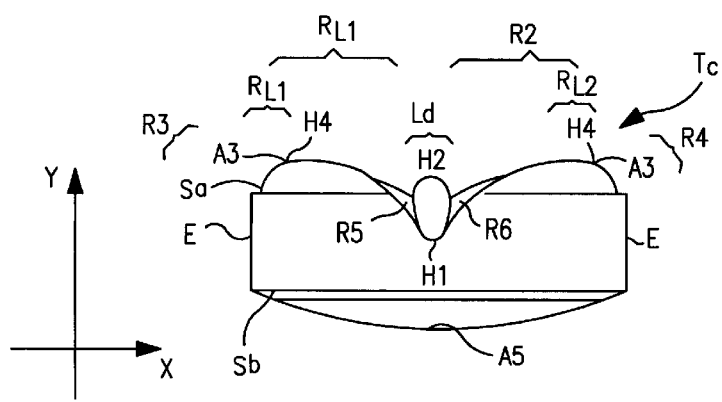

FIGS. 6A to 6C are schematic diagrams of another example of a dividable tablet according to the present invention. FIG. 6A is a plan view, FIG. 6B is a bottom view and FIG. 6C is a side view.

This dividable tablet Tc differs from the dividable tablet Ta in that the dividing line Ld is a U-shaped groove unlike the V-shaped groove of the dividable tablet Ta.

Since the dividing line Ld is a U-shaped groove in this dividable tablet Tc, the thickness of the tablet Tc gradually increases from the deepest portion Ld1 of the dividing line Ld toward the lines Ld2 and Ld2 which are the borders of the dividing line Ld and sharply increases in the vicinity of each of the lines Ld2 and Ld2 which are the borders of the dividing line Ld.

Since the two areas R1 and R2 from the lines Ld2 and Ld2 which are the borders of the dividing line Ld to the ridgelines L1 and L2 have a convex surface in this dividable tablet Tc, the thickness of the tablet Tc sharply increases in the vicinity of each of the lines Ld2 and Ld2 which are the borders of the dividing line Ld in directions from the lines Ld2 and Ld2 to the ridgelines L1 and L2.

Thus, changes in the thickness of the tablet Tc within the area of the dividing line Ld are made greatly different from changes in the thickness of the tablet Tc in the vicinity of each of the lines Ld2 and Ld2 which are the borders of the dividing line Ld in directions from the lines Ld2 and Ld2 to the ridgelines L1 and L2, the thickness of the tablet Tc in the vicinity of each of the lines Ld2 and Ld2 which are the borders of the dividing line Ld in directions from the lines Ld2 and Ld2 to the ridgelines L1 and L2 is sharply increased, and force applied to the tablet Tc from the outside per unit volume is made large within the area of the dividing line Ld and smaller in the vicinity of each of the lines Ld2 and Ld2 which are the borders of the dividing line Ld in directions from the lines Ld2 and Ld2 to the ridgelines L1 and L2 than force applied to the tablet Tc from the outside per unit volume within the area of the dividing line Ld. Therefore, when the tablet Tc is divided into two, it can be divided along the dividing line Ld nicely.

Since the other portions of this dividable tablet Tc are the same as that of the dividable tablet Ta in shape, corresponding portions are given the same reference symbols and their descriptions are omitted.

Figure 7A:
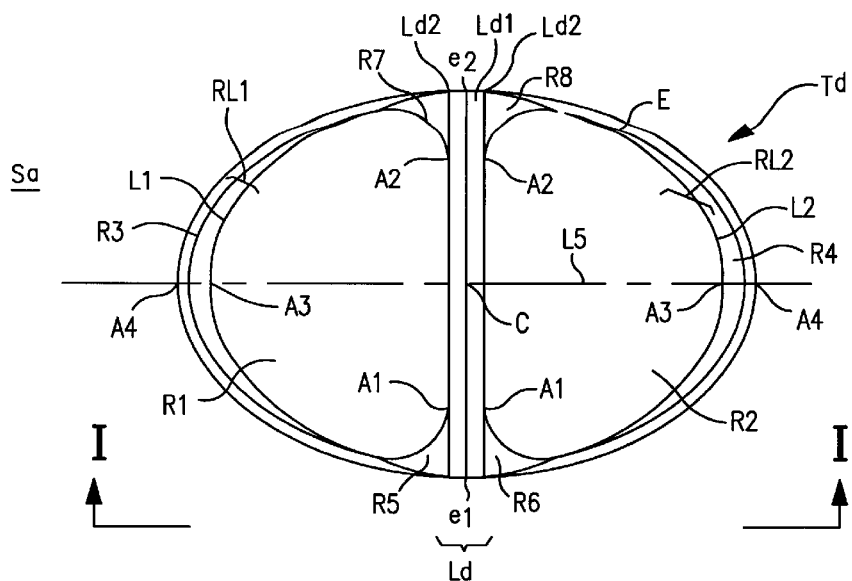
Figure 7B:
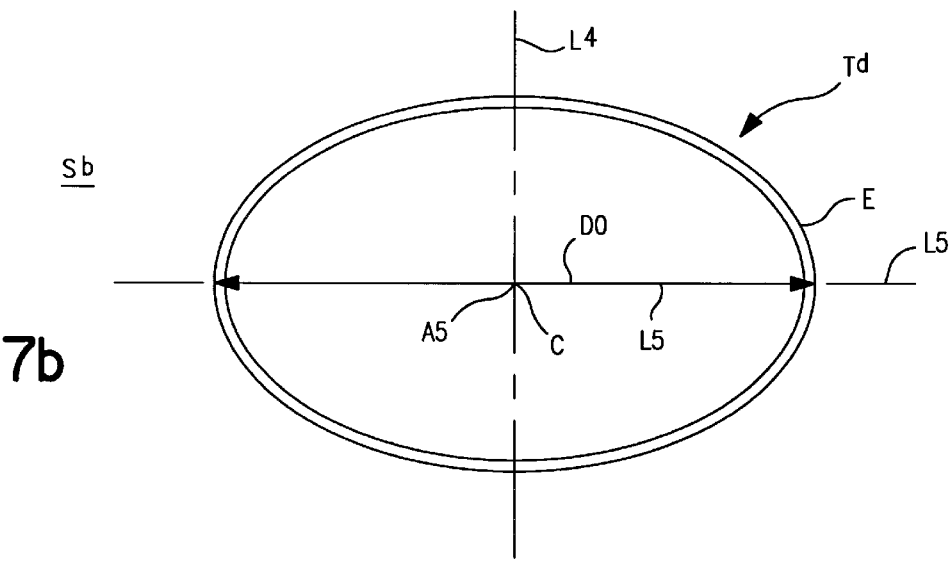
Figure 7C:
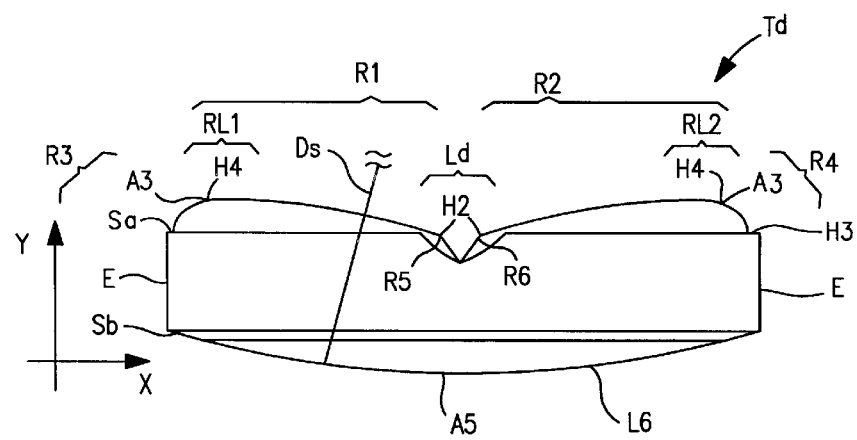

FIGS. 7A to 7C are schematic diagrams of another example of a dividable tablet according to the present invention. FIG. 7A is a plan view, FIG. 7B is a bottom view and FIG. 7C is a side view.

This dividable tablet Td differs from the dividable tablet Ta in that the shape of the tablet Td is oval when seen from above (see FIG. 7A) unlike the round shape of the dividable tablet Ta when seen from above (see FIG. 1A).

In this dividable tablet Td, the dividing line Ld is formed along a short axis L4.

In the case where the shape of the tablet is oval when seen from above, the ratio of the radius (radius Ds shown in FIG. 7C) of the curve L6 of the bottom surface to the long diameter (length of a long axis L5) (long diameter Do of the tablet Td shown in FIG. 7B) of the tablet Td is preferably in the range of 1.25 to 2.5.

This dividable tablet Td has the same effect as that of the dividable tablet Ta. Further, since the shape of the dividable tablet Td is oval when seen from above and the dividing line Ld is formed along the short axis L4, each of the distances from the dividing line Ld in the two areas R1 and R2 defined by the dividing line Ld to points of intersection A4 and A4 between the peripheral portion E of this tablet Td and the long axis L5 is Do/2 which is half the long diameter. Since moment for dividing the tablet Td into two with a finger or the like can be thereby made large, the tablet Td can be divided into two without increasing the strength of the finger or the like.

In this example, the dividing Ld is formed along the short axis L4. It is needless to say that the dividing line Ld may be formed along the long axis L5.

Since the other portions of the dividable tablet Td are the same as those of the dividable tablet Ta in shape, corresponding portions are given the same reference symbols and their descriptions are omitted.

The above dividable tablets Ta, Tb, Tc and Td have areas R5, R6, R7 and R8 which are chamfered into a convex surface in vicinity of points of intersection e1 and e2 between the peripheral portions E of the dividable tablets Ta, Tb, Tc and Td and the dividing line Ld, respectively. Although the areas R5, R6, R7 and R8 which are chamfered into a convex surface are not always required, when the areas R5, R6, R7 and R8 which are chamfered into a convex surface are formed as in the dividable tablets Ta, Tb, Tc and Td, chipping more hardly occurs during the production or transportation of the dividable tablets Ta, Tb, Tc and Td (this was found by the inventor of the present invention and the like from the following Experiment 1 and Experiment 2).

Figure 8A:
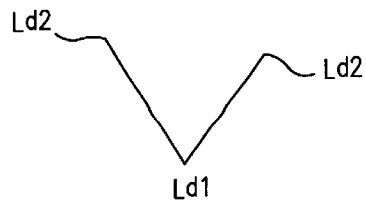
FIGS. 8A to 8E are schematic diagrams showing the preferred shapes of dividing lines formed in dividable tablets according to the present invention.
Figure 8B:
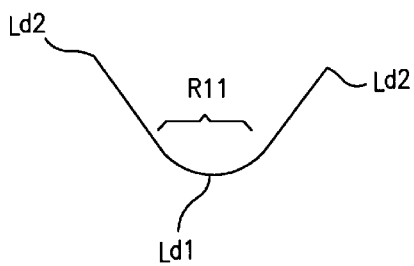
Figure 8C:
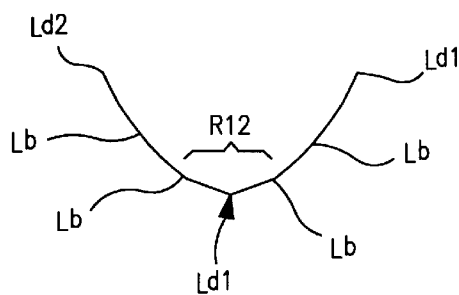
Figure 8D:
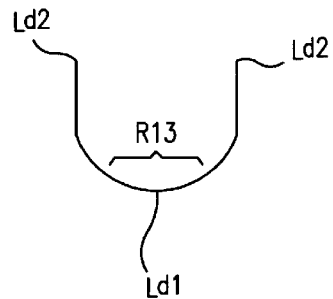
Figure 8E:
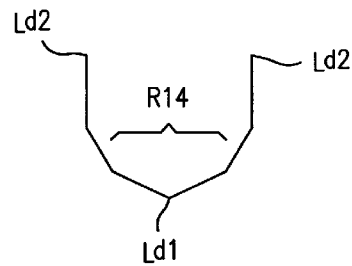

In the above dividable tablets Ta, Tb, Tc and Td, the dividing line Ld is a V-shaped groove or a U-shaped groove. The dividing line formed in the dividable tablet of the present invention may be a V-shaped groove shown in FIG. 8A or a U-shaped groove shown in FIG. 8D. It may have a shape with a round portion R11 in the vicinity of the apex angle of the V-shaped groove or a parabolic shape (a curve of secondary degree) as shown in FIG. 8B, a polygonal shape with at least one bent Lb and not a smooth curve for the round portion R11 in the vicinity of the apex angle of the V-shaped groove as shown in FIG. 8C (see the area R12 shown in FIG. 8C), or a polygonal shape with at least one bent Lb and not a smooth curve (see the area R13 shown in FIG. 8D) for the round portion at a lower portion of an ordinary U-shaped groove as shown in FIG. 8E (see the area R14 shown in FIG. 8E).

When the dividing line Ld is made polygonal with at least one bent Lb and the dividable tablet is to be divided into two, force is concentrated on either one of the bents Lb, and the tablet is easily divided into two along either one of the bents Lb, thereby making it possible to divide the tablet along the dividing Ld more nicely.

In the dividable tablets Ta, Tb, Tc and Td, the steep slopes R3 and R4 from the ridgelines L1 and L2 on the upper surfaces Sa of the tablets Ta, Tb, Tc and Td to the peripheral portions E of the tablets Ta, Tb, Tc and Td are each formed by a convex surface when seen from side. The steep slopes R3 and R4 may be formed by a plane surface when seen from side.

In this case, joint portions between the convex (gently rising) areas R1 and R2 from the lines Ld2 and Ld2 which are the borders of the dividing line Ld on the upper surfaces of the tablets Ta, Tb, Tc and Td to the ridgelines L1 and L2 and the steep slopes R3 and R4 having plane surfaces when seen from side are preferably located at positions lower than the heights in a vertical direction of the ridgelines L1 and L2 toward the peripheral portions E of the tablets Ta, Tb, Tc and Td from the ridgelines L1 and L2 and not at the ridgelines L1 and L2 to prevent the chipping of the tablets.

In the dividable tablet of the present invention, whether the steep slopes from the ridgelines on the upper surface of the tablet to the peripheral portion of the tablet should have a plane surface or a convex surface can be determined from the design of the tablet.

Therefore, the shape of the dividable tablet of the present invention can be determined so that it can impress a doctor, pharmacist, patient or the like based on the medical virtue, efficacy and effect thereof.

Stated more specifically, for example, if the shape of the area from the line which is the border of the dividing line on the upper surface of the tablet to the ridgeline is made linear when seen from side, the whole tablet can give an observer a sharp impression. Therefore, the product of the tablet is characterized by this sharp impression. For example, when the tablet is used for oral antibiotic formulations and pain-killing antiphlogistic agents, these formulations can give an observer a sharp impression.

Alternatively, if the shape of the area from the line which is the border of the dividing line on the upper surface of the tablet to the ridgeline is made a gentle curve when seen from side, the whole tablet can give an observer a mild impression. Therefore, the product of the tablet is characterized by its mild function and effect and little side effect. For example, when the tablet is used for medicines which work on the circulatory system such as a hypotensive drug and medicines which work on the central nervous system such as a narcotic and a sedative, the mild function and effect and little side effect of these formulations can impress an observer.

The present invention will be described hereinunder based on specific experimental data.

(Experiment 1)

67.5 wt % of lactose (200M of DMV Co.) and 29.0 wt % of corn starch (Nisshoku Corn Starch W of Nippon Shokuhin Kako Co.) were charged into a fluidized-bed granulating machine (Flow Coater FLO-15 of Furoin Co.), a 7 wt % aqueous solution of hydroxypropyl cellulose (HPC-L of Nippon Soda Co.) was prepared as a binder and sprayed onto the resulting powders, the resulting powders were granulated and dried to give dry powders. The dry powders contained 3 wt % of the binder.

The thus produced dry powders were shaped by a sizer (Randel Mill RM-I of Tokuju Kosakusho Co.), 0.5 wt % of a lubricant (magnesium stearate of Sakai Kagaku Co.) was added to the obtained shaped product and mixed with a blender (Mix Well Mixer V1-60 of Tokuju Kosakusho Co.) for 5 minutes to give a molding material.

Figure 9A:
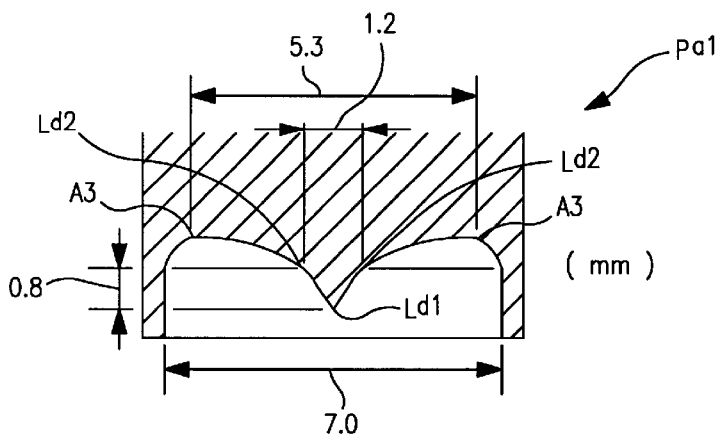
FIGS. 9A to 9C are schematic diagrams showing the shapes of upper punches used in experiments to produce dividable tablets according to the present invention.
Figure 9B:
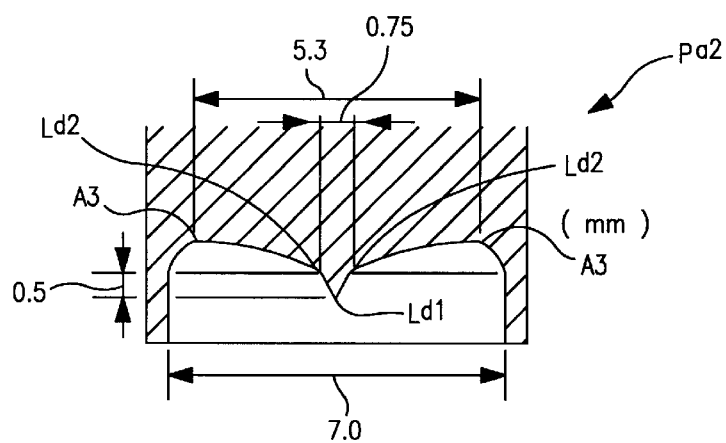
Figure 9C:
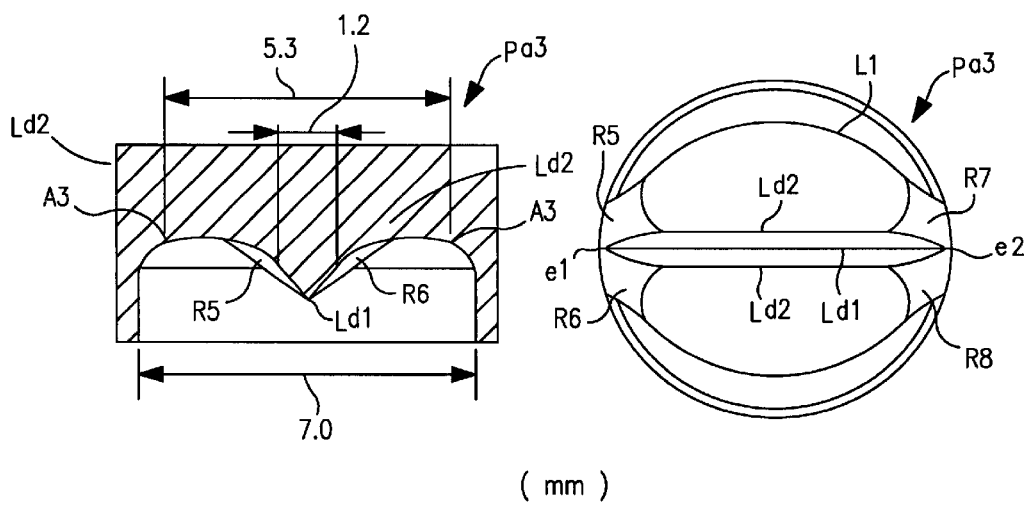
Figure 10A:
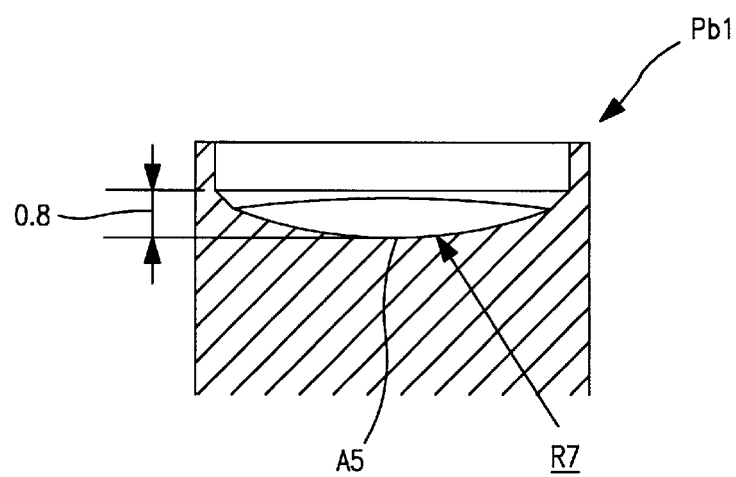
FIGS. 10A and 10B are schematic diagrams showing the shapes of lower punches used in experiments to produce dividable tablets according to the present invention.
Figure 10B:
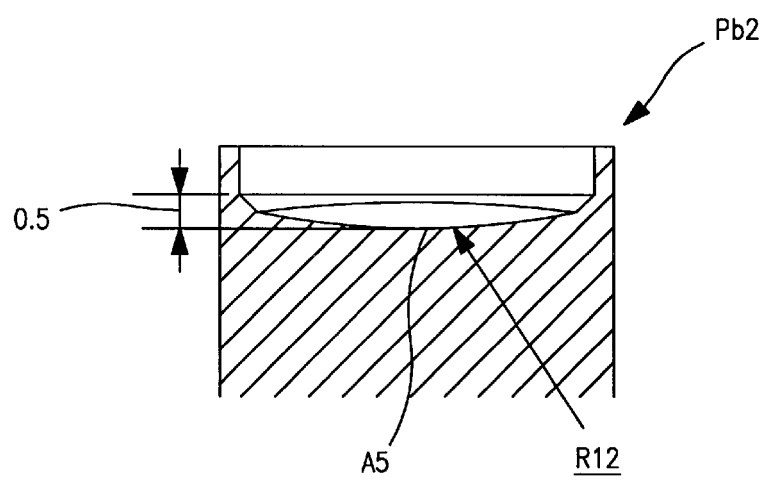

To produce the dividable tablet of the present invention, upper punches pa1, pa2 and pa3 shown in FIGS. 9A to 9C and lower punches pb1 and pb2 shown in FIGS. 10A and 10B were fabricated.

The upper punches pa1 and pa2 were used to produce dividable tablets in which chamfered areas (R5, R6, R7 and R8 shown in FIGS. 1A to 1C) were not formed in the vicinity of the point of intersection between the dividing line Ld and the peripheral portion of the tablet and the upper punch pa3 was used to produce dividable tablets in which chamfered areas (R5, R6, R7 and R8 shown in FIGS. 1A to 1C) were formed in the vicinity of the point of intersection between the dividing line Ld and the peripheral portion of the tablet.

The upper punches pa1, pa2 and pa3 are molds having the shape of the upper surface of a dividable tablet to be molded and the lower punches pb1 and pb2 are molds having the shape of the lower surface of a dividable tablet to be molded.

In FIGS. 9A to 9C and FIGS. 10A and 10B, portions corresponding to the portions of the dividable tablet of the upper punches pa1, pa2 and pa3 and the lower punches pb1 and pb2 are given the same reference symbols and the sizes of the produced upper punches pa1, pa2 and pa3 and the lower punches pb1 and pb2 are provided.

A combination of the upper punch pa1 and the lower punch pb1 was set in a high-speed rotary tabletting machine (VIRGO12 of Kikusui Seisakusho Co.) to tablet the molding material produced above.

A combination of the upper punch pa1 and the lower punch pb2, a combination of the upper punch pa2 and the lower punch pb1 and a combination of the upper punch pa2 and the lower punch pb2 were each set in the high-speed rotary tabletting machine (VIRGO12 of Kikusui Seisakusho Co.) to tablet the molding material produced above.

Four different dividable tablets in total of the present invention were produced in accordance with the above process.

The weight of each tablet was 130 mg.

These four different tablets were each divided into two on a flat table by 5 panelists chosen arbitrarily (three men (M) and two women (W)) while the dividing line faced up or down and the ease of division at this point was evaluated by an organoleptic test.

As for evaluation, 3 points were given to a tablet which was easily divided, 2 points to a tablet which was hardly divided, 1 point to a tablet which was extremely hardly divided and 0 point to a tablet which could not be divided. 15 points in total were a perfect score.

As comparative example, a commercially available upper KARATE shape and lower standard concave tablet (trade name: Norpasuku Tablet of Pfizer Seiyaku Co.) was divided in the same manner, and division ease at this point was evaluated based on four criteria by an organoleptic test.

The results are shown in Table 1.

TABLE 1

|  | shape of upper punch | shape of lower punch | Direction of Division | panelists | | | | | total number of points |
|---|---|---|---|---|---|---|---|---|---|
|  |  |  |  | W1 | M1 | W2 | M2 | M3 |  |
| Examples | pa1 | pb1 | Upper | 3 | 3 | 3 | 3 | 3 | 15 |
|  |  |  | Lower | 1 | 2 | 2 | 2 | 3 | 10 |
|  |  | pb2 | Upper | 3 | 3 | 3 | 3 | 3 | 15 |
|  |  |  | Lower | 1 | 3 | 2 | 3 | 3 | 10 |
|  | pa2 | pb1 | Upper | 3 | 3 | 3 | 3 | 3 | 15 |
|  |  |  | Lower | 2 | 2 | 2 | 2 | 2 | 10 |
|  |  | pb2 | Upper | 3 | 3 | 3 | 3 | 3 | 15 |
|  |  |  | Lower | 1 | 2 | 1 | 3 | 3 | 10 |
| Comparative Example | upper KARATE shape and lower standard concave tablet (trade product) | | Upper | 2 | 2 | 1 | 1 | 1 | 9 |
|  |  |  | Lower | 2 | 1 | 1 | 3 | 3 | 10 |

In Table 1, the direction of division shows whether the dividing line of the tablet faces up or down.

It is revealed from Table 1 that the four different dividable tablets of the present invention are much more easily divided than that of comparative example (trade name: Norpasuku tablet of Pfizer Seiyaku Co.) when the dividing line Ld faces up.

It is also found that when the dividing line Ld faces down, it is more difficult to divide the tablet of the present invention than that of comparative example.

(Experiment 2)

To further improve the four different dividable tablets of the present invention which were divided nicely in the organoleptic test of Experiment 1, the upper punch pa3 shown in FIG. 9C and the lower punch pb2 shown in FIG. 10B were used in conjunction to produce the dividable tablet of the present invention in the same manner as in Experiment 1.

Figure 11A:
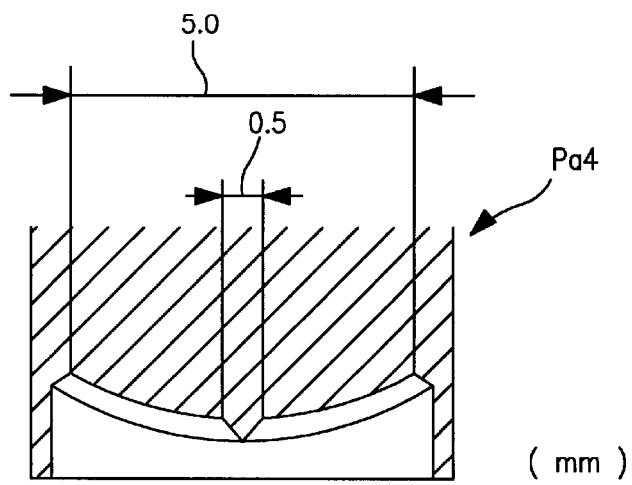
FIGS. 11A and 11B are schematic diagrams showing the shapes of an upper punch and a lower punch used in an experiment to produce a conventionally known upper KARATE shape and lower standard concave tablet.
Figure 11B:
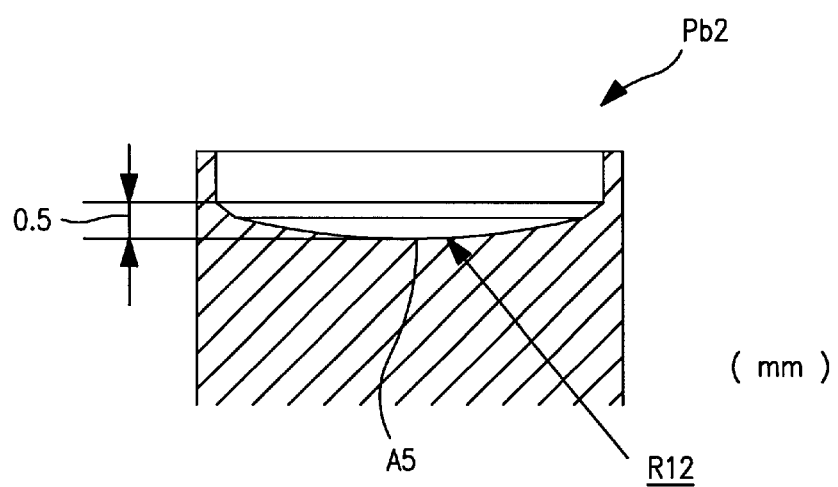

As comparative example, a conventionally known upper KARATE shape and lower standard concave tablet was produced using a combination of an upper punch pa4 and the lower punch pb2 shown in FIGS. 11A and 11B in the same manner as in Experiment 1.

Then, a drop test was made on the obtained dividable tablets.

The drop test was carried out as follows. 100 dividable tablets of the present invention and 100 tablets of comparative example (upper KARATE shape and lower standard concave tablets) were dropped onto a stainless steel plate, chipped portions were observed and the number of chipped tablets was counted visually.

Figure 12A:
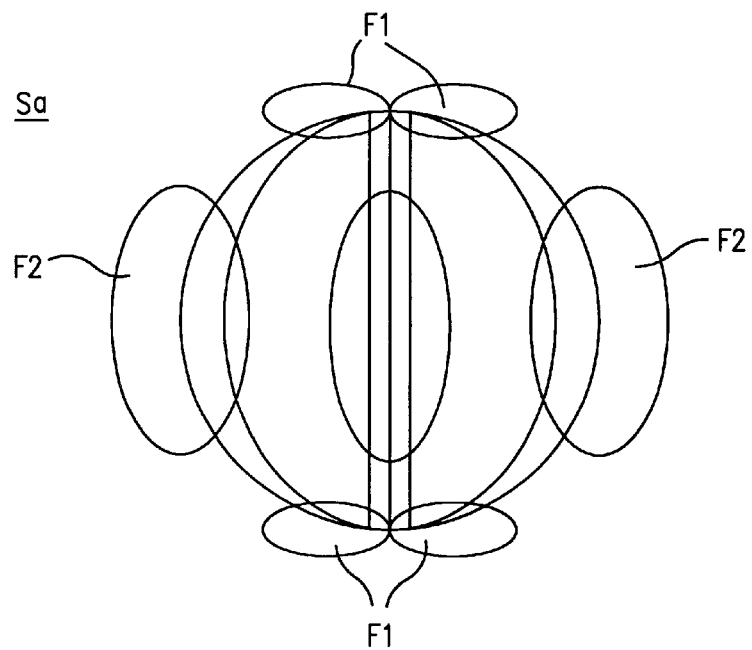
Figure 12B:
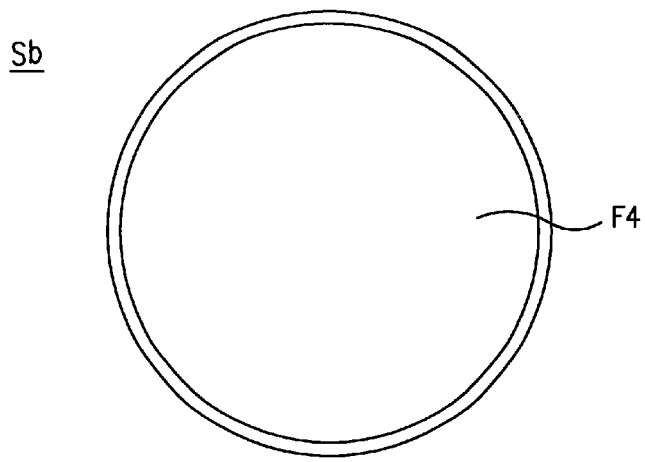
Figure 13A:
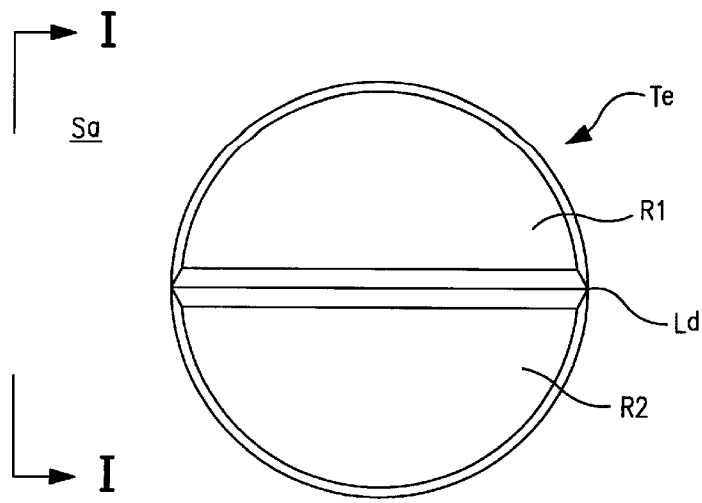
Figure 13B:
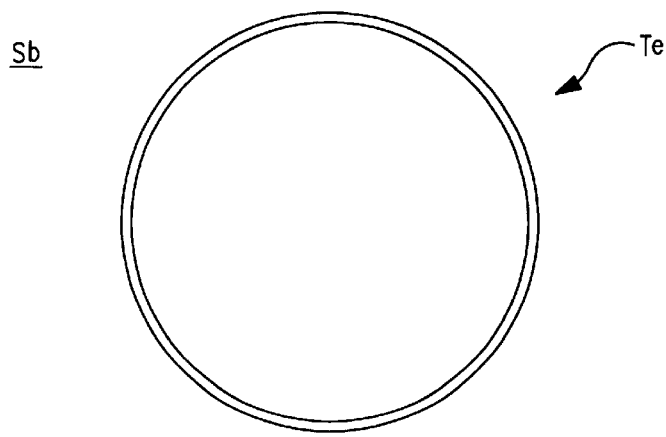
Figure 13C:
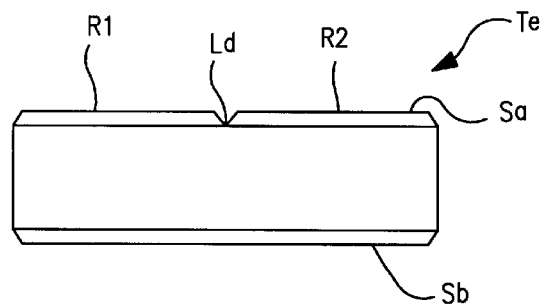
Figure 14A:
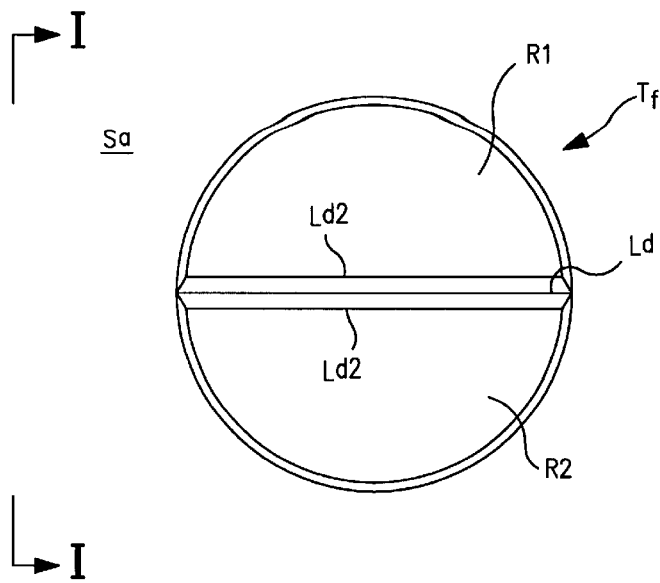
Figure 14B:
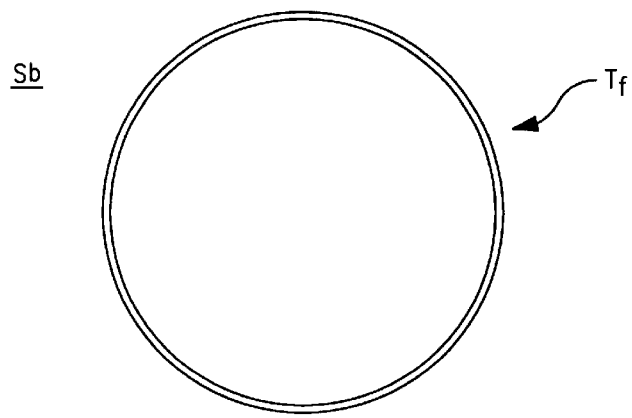
Figure 14C:
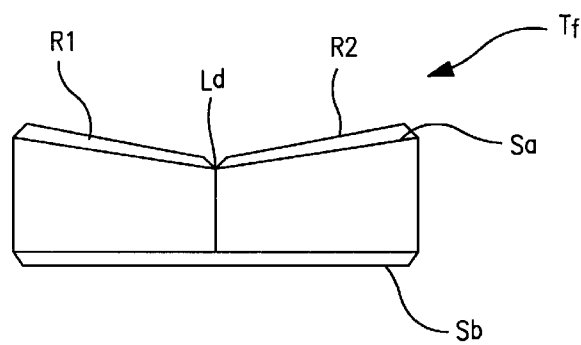
Figure 15A:
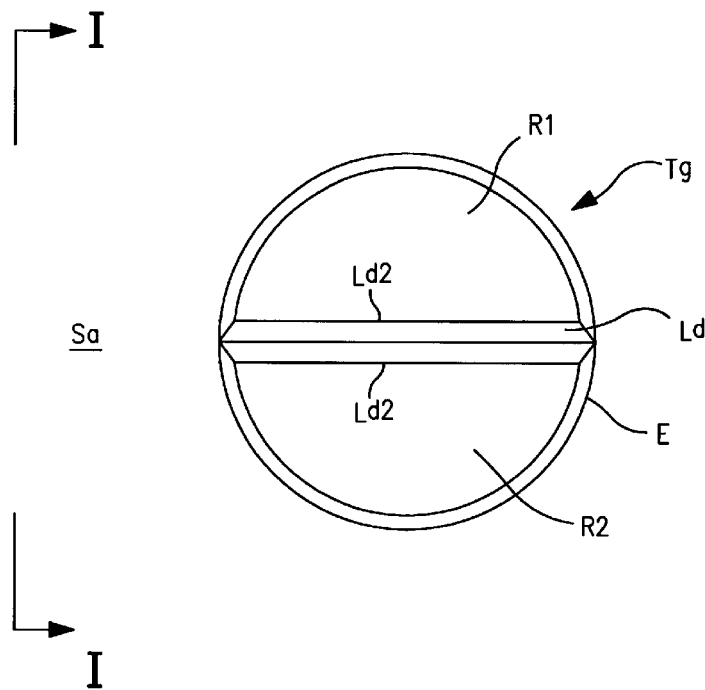
FIG. 15A is a plan view.
Figure 15B:
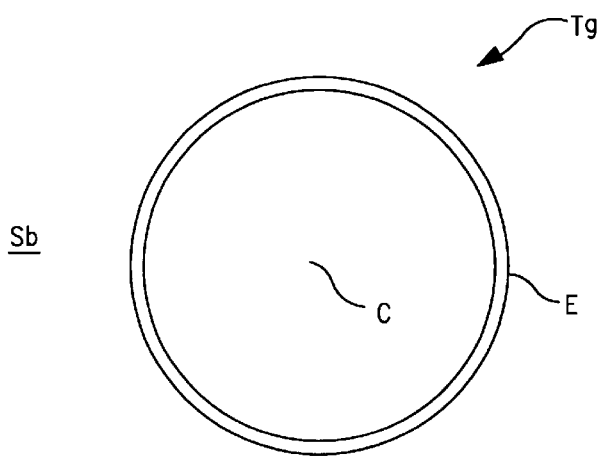
FIG. 15B is a bottom view and FIG. 15C is a side view along line I—I of FIG. 15A.
Figure 15C:
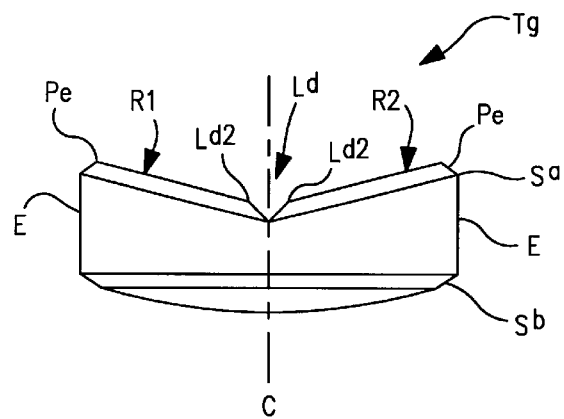
Figure 16A:
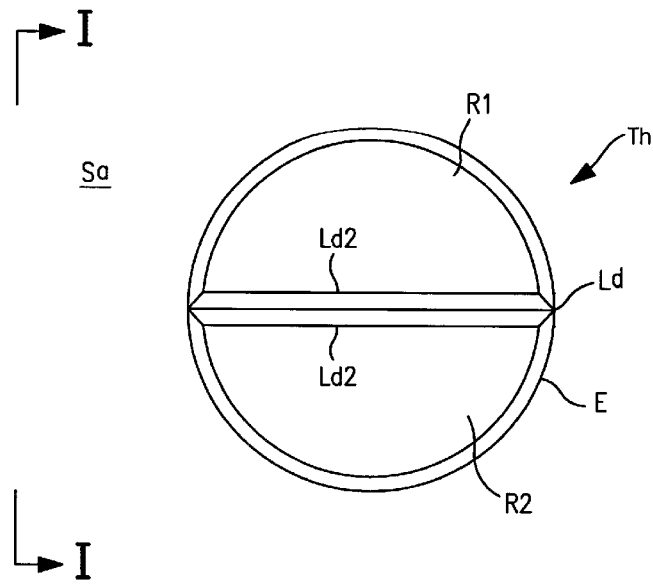
Figure 16B:
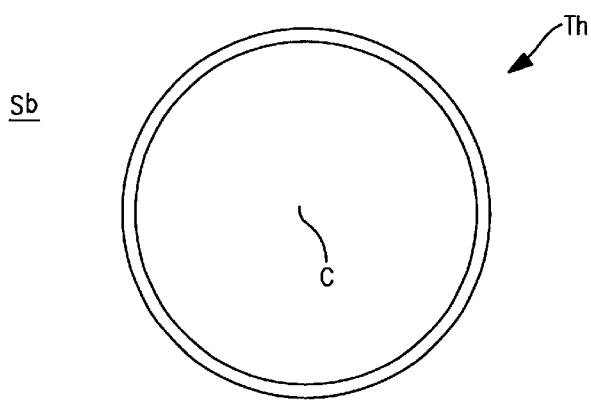
Figure 16C:
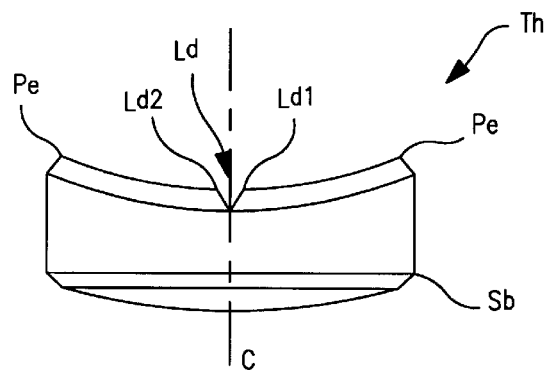
Figure 17:
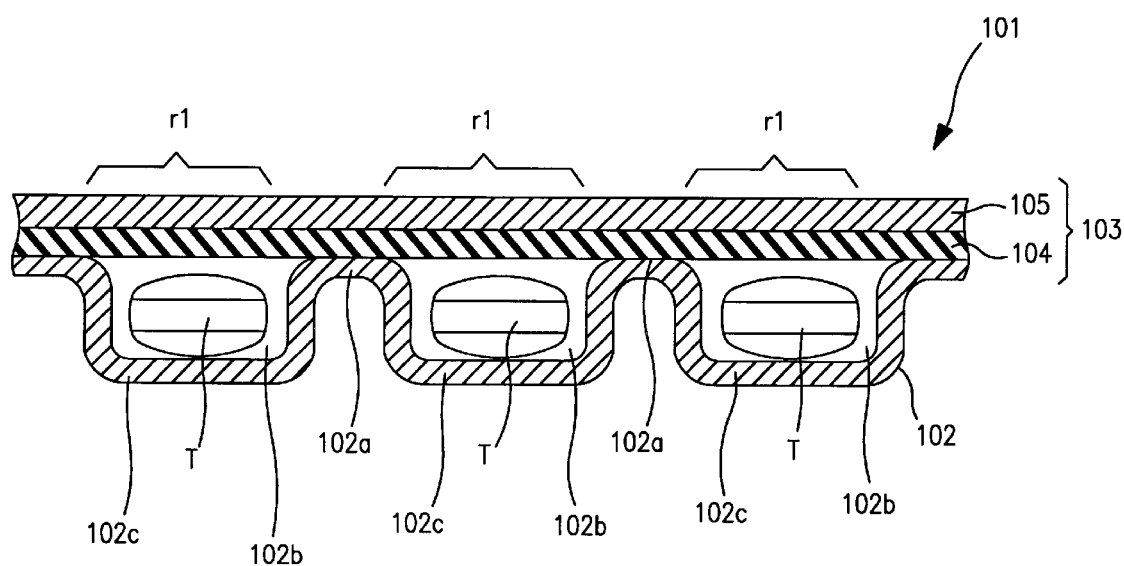
FIG. 17 is a sectional view typically showing an example of a press-through pack of the prior art.
Figure 18A:
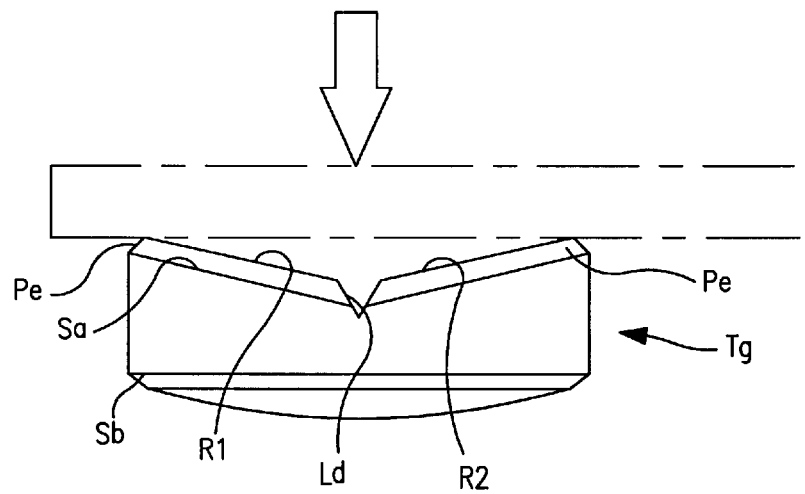
Figure 18B:
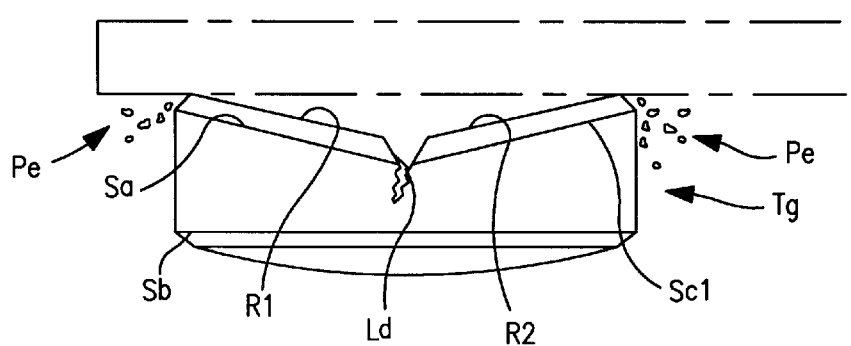
Figure 19A:
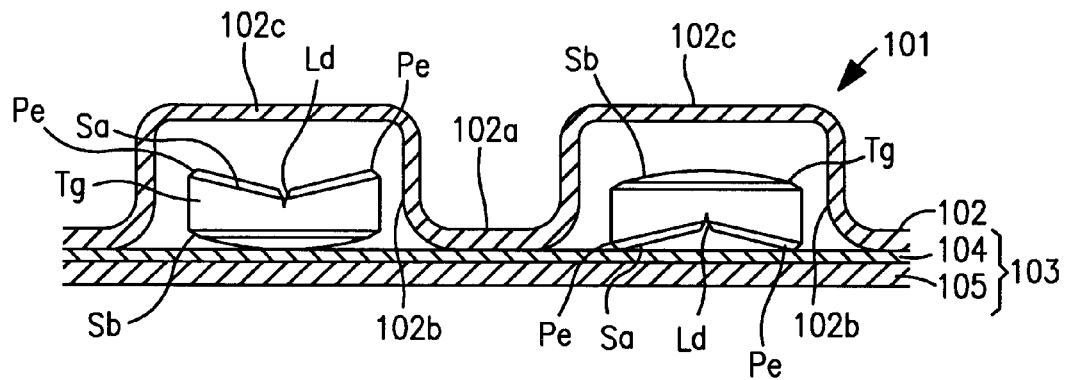
Figure 19B:
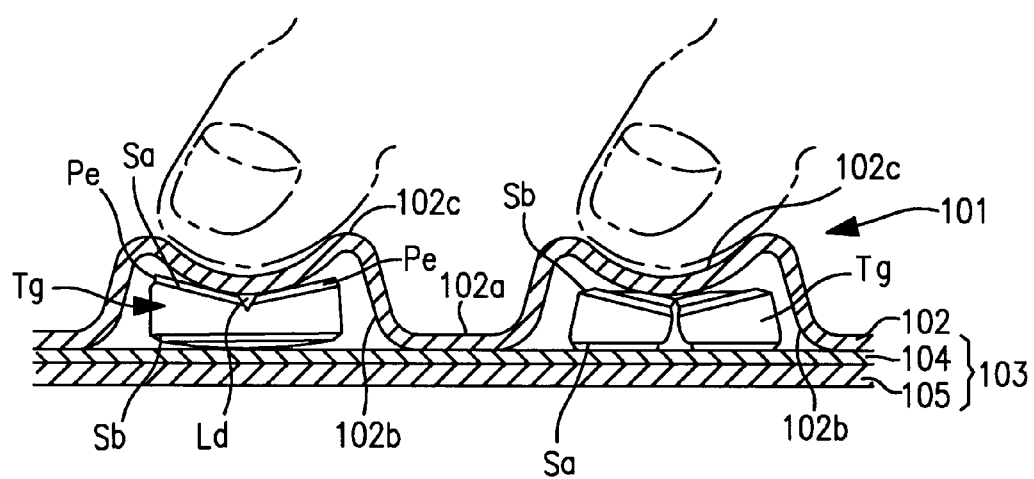
Figure 20A:
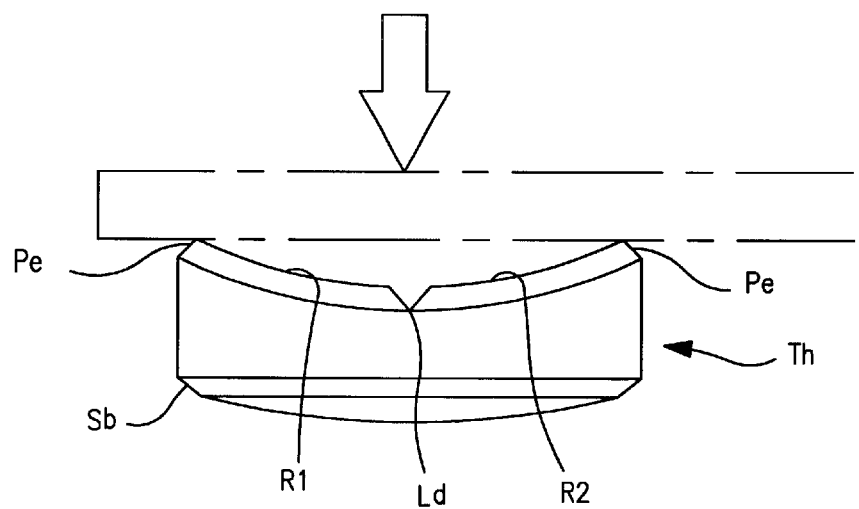
Figure 20B:
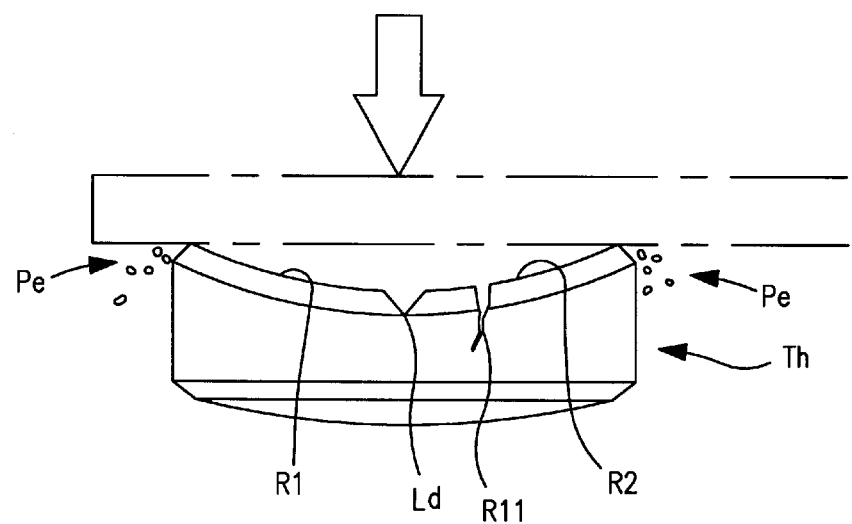
Figure 21A:
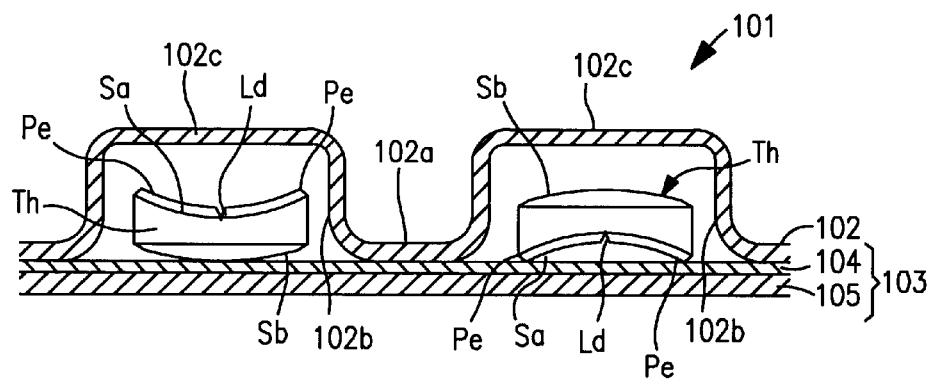
Figure 21B:
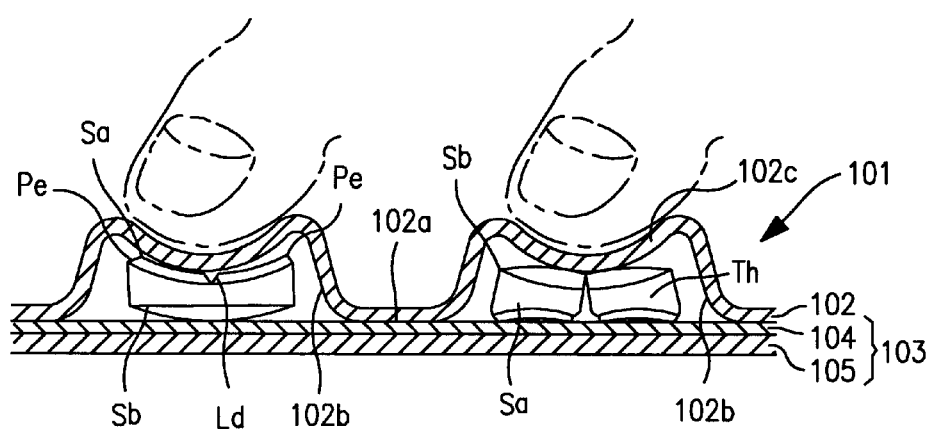

The observation sites of the chipped portions were F1, F2 and F3 on the upper surface Sa of the dividable tablet shown in FIG. 12A and F4 on the lower surface Sb of the dividable tablet shown in FIG. 12B.

The results of the drop test are shown in Table 2.

the lower punch pb2 shown in FIG. 10B in the same manner as in Example 1.

As comparative example, a conventionally known upper KARATE shape and lower standard concave tablet was produced using the upper punch pa4 shown in FIG. 11A and the lower punch pb1 shown in FIG. 10A in the same manner as in Experiment 1.

An abrasion test was made on the obtained dividable tablets.

The abrasion test was carried out after 20 dividable tablets of the present invention and 20 tablets of comparative example (upper KARATE shape and lower standard concave tablet) were placed in a fly ablator and rotated at 25 rpm for 10 or 20 minutes.

The results of the abrasion test are shown in Table 3.

TABLE 3

|  | Example | | upper KARATE shape and lower standard concave tablet | |
| --- | --- | --- | --- | --- |
| upper punch | pa3 | | pa4 | |
| lower punch | pb1 | pb2 | pb1 | pb2 |
| 10 minutes | 0.25% | 0.15% | 0.54% | 0.49% |
| 20 minutes | 0.49% | 0.52% | 1.14% | 1.06% |

It is understood from Table 3 that the abrasion of the dividable tablets of the present invention is about half that of the dividable tablets of comparative example (upper KARATE shape and lower standard concave tablet).

(Experiment 4)

A coating solution (aqueous solution of OPADRY-II (OY-LS-22813 of Karakon Co.)) was coated on 1 kg of dividable tablets of the present invention produced in Experiment 3 using a coating machine (HCT-30N of Furoint Co.).

A coating solution (aqueous solution of OPADRY-II (OY-LS-22813 of Karakon Co.)) was coated on 1 kg of the conventionally known dividable tablets produced as com-

TABLE 2

| | | | | First drop | | | second drop | |
| --- | --- | --- | --- | --- | --- | --- | --- | --- |
| | Upper punch | lower punch | Site | number of chipped tablets | total number of chipped tablets | site | number of chipped tablets | total number of chipped tablets |
| Example | pa3 | pb2 | F1 | 1 | 1 out of 100 | F1 | 4 | 4 out of 100 |
| | | | F2 | 0 | | F2 | 0 | |
| | | | F3 | 0 | | F3 | 0 | |
| | | | F4 | 0 | | F4 | 0 | |
| Comparative Example | pa4 | pb2 | F1 | 0 | 4 out of 100 | F1 | 0 | 13 out of 100 |
| | | | F2 | 4 | | F2 | 12 | |
| | | | F3 | 0 | | F3 | 0 | |
| | | | F4 | 0 | | F4 | 1 | |

It is understood from Table 2 that the number of the chipped dividable tablets of the present invention is much smaller than that of comparative example (upper KARATE shape and lower standard concave tablets).

When the type of chipping was investigated, the number of dividable tablets whose edges were chipped was especially reduced.

(Experiment 3)

The dividable tablet of the present invention was produced using the upper punch pa3 shown in FIG. 9C and the lower punch pb1 shown in FIG. 10A in the same manner as in Experiment 1.

The dividable tablet of the present invention was also produced using the upper punch pa3 shown in FIG. 3C and parative example in Experiment 3 using a coating machine (HCT-30N of Furoint Co.).

As a result, twinning did not occur in the dividable tablets of the present invention and the peel-off of coating films caused by twining was not seen.

(Experiment 5)

It was tested whether a large number of the dividable tablets of the present invention could be divided when they were wrapped in a press-through pack.

The dividable tablets (coated) of the present invention produced in Experiment 4 were contained in the storage recessed portions of the press-through pack.

10 dividable tablets (coated) of the present invention which were contained in the storage recessed portions of the press-through pack and whose dividing lines faced up and 10 dividable tablets (coated) of the present invention whose dividing lines faced down were divided into two with a finger without being taken out from the storage recessed portions, and the divided tablets were each weighed by a chemical balance to obtain the weight change coefficient of each of the dividable tablets (coated) of the present invention after they were divided into two.

As comparative example, 10 dividable tablets (coated) of the present invention whose dividing lines faced up and 10 dividable tablets (coated) of the present invention whose dividing lines faced down were cut along the dividing lines using a commercially available tablet cutter (of Kobayashi Seiyaku Co.), and the divided tablets were each weighed by a chemical balance to obtain the weight change coefficient of each of the tablets of the present invention after they were divided into two.

The results are shown in Table 4.

TABLE 4

| lower punch | direction of dividing line | |
| --- | --- | --- |
| | up | down |
| Pb1 | 2.5% | 2.1% |
| Pb2 | 2.2% | 1.8% |
| tablet cutter | 1.9% | |

It is understood from Table 4 that the weight change coefficient of the dividable tablet of the present invention after it is divided into two is almost the same as that of the tablet after it is divided along the dividing line by the tablet cutter whether the dividing line faces up or down. Thereby, it is made clear that the dividable tablet of the present invention can be divided into two accurately with a finger whether the dividing line faces up or down.

Further, this experiment reveals that the tablet produced using the lower punch pb2 having a larger radius of curvature than that of the lower punch pb1 has a smaller change coefficient than that of the tablet produced using the lower punch pb1. This is probably because the broken area at the time of division is small.

(Experiment 6)

The dividable tablets of the present invention produced in Experiment 2 were wrapped in a press-through pack and hardness required for division was measured with a tablet hardness measuring instrument (PTB-311/P of Japan Machinery Co.) while they were contained in the storage recessed portions of the press-through pack.

As comparative example, commercially available upper KARATE shape and lower standard concave tablets (Norpasuku of Pfizer Seiyaku Co.) were used to measure hardness required for division with a tablet hardness measuring instrument (PTB-311/P of Japan Machinery Co.) while they were contained in the storage recessed portions of the press-through pack.

The press-through pack used in comparative example was identical to the press-through pack used to contain the dividable tablets of the present invention and the wrapping method of comparative example was the same as that for wrapping the dividable tablets of the present invention in the press-through pack.

The results are shown in Table 5.

TABLE 5

| | upward force | downward force |
| --- | --- | --- |
| Example | 25 N | 26 N |
| upper KARATE shape and lower standard concave tablet (trade product) | 106 N | 102 N |

It is understood from Table 5 that the dividable tablet of the present invention can be divided with force about ¼ that of Comparative example.

It is obvious from the above results that the dividable tablet of the present invention has such a shape that it can be more easily divided than the dividable tablet of the prior art.

According to the first aspect of the present invention, the areas around the two ridgelines are each formed by a convex surface to eliminate a pointed edge portion from the upper surface of the tablet when the two ridgelines are formed in two areas defined by the dividing line on the upper surface of the tablet. Therefore, when force is applied to the tablet from above in a vertical direction, the tablet can be divided along the dividing line nicely without being chipped. Further, the tablet is hardly chipped in the tabletting step, during pneumatically transportation or when it is transported in a press-through pack or in a bottle.

Since a pointed edge portion is eliminated from the upper surface of the tablet, core erosion, edge chipping or the like hardly occurs in the coating step.

Since a pointed edge portion is eliminated from the upper surface of the tablet, when the tablet is contained in the storage recessed portion of a press-through pack, the sealing sheet is hardly broken by the tablet.

According to the second aspect of the present invention, the lower surface of the tablet gradually rises from the peripheral portion of the tablet toward the center portion thereof. Therefore, when the upper surface having the dividing line of the tablet contained in the storage recessed portion of the storage body of the press-through pack faces the sealing sheet, the tablet can be easily divided into two by pressing the protuberant center portion of the lower surface of the tablet with a finger through the projecting portion which is the exterior surface of the storage recessed portion of the storage body of the press-through pack.

Since the areas from the lines which are the borders of the dividing line to the two ridgelines are each formed by a convex surface, even when the side having the dividing line of the tablet contained in the storage recessed portion of the press-through pack faces the storage body, force is applied to the tablet in the direction for opening the dividing line without increasing the strength of the finger compared with the dividable tablet of the prior art because the two areas defined by the dividing line on the upper surface of the tablet have a curved surface corresponding to the shape of the storage recessed portion to be crushed substantially into a V shape when seen from side and the shape of the finger when the projecting portion which is the exterior surface of the storage recessed portion of the press-through pack is pressed with the finger. Thereby, even when the side having the dividing line of the tablet contained in the storage recessed portion of the press-through pack faces the storage body, the tablet can be easily divided into two.

Thus, when this dividable tablet is contained in the storage recessed portion of the storage body of the press-through pack without limiting the direction of the tablet, it can be divided into two before it is taken out from the press-through pack. Thereby, there can be provided a press-through pack which enables the dividable tablet contained in the storage recessed portion to be easily divided into two before it is taken out from the storage recessed portion of the press-through pack.

Since this dividable tablet has two convex surfaces on the upper side and one convex surface on the lower side, the tablets are not face contacted to each other but point contacted to each other. Thereby, twining hardly occurs in the coating step.

According to the third aspect of the present invention, since the dividing line of the tablet is formed deeper than that of an ordinary dividable tablet, the tablet can be divided along the dividing line nicely.

According to the fourth aspect of the present invention, since changes in the thickness of the tablet within the area of the dividing line are made greatly different from changes in the thickness of the tablet in the vicinity of each of the lines which are the borders of the dividing line in directions from these lines to the ridgelines, the thickness of the tablet in the vicinity of each of the lines which are the borders of the dividing line in directions from these lines to the ridgelines is sharply increased, and force to be applied from the outside of the tablet per unit volume is made large within the area of the dividing line and smaller in the vicinity of each of the lines which are the borders of the dividing line in directions from these lines to the ridgelines than force to be applied from the outside of the tablet per unit volume within the area of the dividing line. Therefore, this tablet can be divided into two along the dividing line nicely.

According to the fifth aspect of the present invention, since the lines which are the borders of the dividing line are formed at positions above the upper surface of the peripheral portion of the tablet and not on the upper surface of the tablet, the dividing line can be made large without forming it deep in the vertical direction of the tablet from the upper surface of the tablet (the depth of the dividing line can be increased). Thereby, the dividing line can be made large (depth of the dividing line can be increased) without weakening the mechanical strength of the tablet in an area where the dividing line is formed as in the case where the dividing line is formed deep in the vertical direction of the tablet from the upper surface of the tablet. Therefore, a dividable tablet which can be easily divided into two and is not divided into two of itself when it is not intended to be divided can be obtained.

According to the sixth aspect of the present invention, the areas from the two ridgelines on the upper surface of the tablet to the peripheral portion of the tablet are each formed by a steep slope and the areas from the lines which are the borders of the dividing line on the upper surface of the tablet to the ridgelines are each formed by a gently rising surface than the above areas. Therefore, when force is applied to the tablet from above in a vertical direction, force is easily applied in a direction for opening the tablet. Thereby, the tablet can be divided nicely along the dividing line with small force.

According to the seventh aspect of the present invention, whether the steep slopes from the ridgelines on the upper surface of the tablet to the peripheral portion of the tablet should have a plane surface or a convex surface may be determined from the design aspect of the tablet. Therefore, based on the medical virtue, efficacy and effect of the dividable tablet, the shape of the tablet can be determined to impress doctors, pharmacists, patients and the like.

According to the eighth aspect of the present invention, the areas in the vicinity of the points of intersection between the dividing line and the peripheral portions of the tablet are chamfered into two convex surfaces sandwiching the dividing line, the tablet is more hardly chipped.

According to the ninth aspect of the present invention, the bonding strength of the adhesive of the press-through pack is controlled by adjusting the adhesive such that the storage body does not peel off or rise from the sealing sheet outside the so-called pocket when a solid is taken out by breaking part of the sealing sheet by pressing the projecting portion which is the exterior surface of the storage recessed portion containing the dividable tablet and that the sealing sheet can be peeled off from the storage body without being broken when part of the sealing sheet is peeled off from the storage body and turned up.

Therefore, this press-through pack enables the dividable tablets wrapped therein to be taken out from the storage recessed portions one by one or at a time by peeling off the sealing sheet from the storage body.

Further, since the above dividable tablets are contained in the storage recessed portions of the press-through pack, even when the dividable tablets are contained in the storage recessed portions without limiting the directions thereof, the dividable tablets can be divided into two easily and simply by pressing the projecting portions which are the exterior portions of the storage recessed portions containing the dividable tablets before they are taken out from the storage recessed portions.

Therefore, the dividable tablets can be divided into two easily and simply before they are taken out from the storage recessed portions and then the divided dividable tablets can be taken out from the storage recessed portions.

Further, before the dividable tablets contained in the storage recessed portions of the press-through pack are taken out from the storage recessed portions, they can be divided into two easily and simply and then the divided dividable tablets contained in the press-through pack can be taken out at a time by peeling off the sealing sheet from the storage body.

Therefore, use of this press-through pack can greatly simplify preparation work at a hospital or the like.

What is claimed is:

1. A dividable tablet comprising:
    a tablet having a dividing line formed along a center line on an upper surface thereof, said dividing line dividing said upper surface into a first portion and a second portion;
    first and second ridgelines, respectively formed in said first portion and said second portion of said upper surface; and
    a bottom portion of said tablet having a top at its center,
    wherein each of said ridgelines has a round surface,
    wherein each of said ridgelines has ends and a middle portion,
    wherein said ends of said ridgelines are located closer to said dividing line than said middle portions,
    wherein said middle portions of said ridgelines are raised above said dividing line to define a peak portion in each of said ridgelines,
    wherein surfaces from said dividing line to each of said ridgelines have a convex round surface respectively, and
    wherein surfaces from a periphery of said tablet to each of said ridgelines are respectively positioned below each of said ridgelines.

2. A dividable tablet comprising:
    a tablet having a dividing line formed along a center line on an upper surface thereof, said dividing line dividing said upper surface into a first portion and a second portion;

first and second ridgelines, respectively formed in said first portion and said second portion of said upper surface; and a bottom portion of said tablet having a top at its center, wherein each of said ridgelines has a round surface, wherein each of said ridgelines has ends and a middle portion, wherein said ends of said ridgelines are located closer to said dividing line than said middle portions, wherein said middle portions of said ridgelines are raised above said dividing line to define a peak portion in each of said ridgelines, wherein surfaces from said dividing line to each of said ridgelines have a convex round surface respectively, and wherein said tablet is divided into two portion by a force which adds to only three points consisting of said top of its center of the bottom portion of said tablet and two summits, each of which is formed by two ridge lines which are located in said first portion and in said second portion which are formed with said dividing line which is provided on an upper surface of said tablet.

3. The dividable tablet as set forth in claim 1 or 2, wherein said middle portions of said ridgelines are respectively located closer to a periphery of said tablet on condition that a length between each of said middle portions and a periphery of said tablet is shorter than a length between each of said middle portions and said dividing line.

4. The dividable tablet of claim 1 or 2, wherein the first portion and the second portion defined by said dividing line on the upper surface of the tablet and extending from lines which are the borders of said dividing line to said two ridgelines are each formed by a convex surface.

5. The dividable tablet of claim 3, wherein the first portion and the second portion defined by said dividing line on the upper surface of the tablet and extending from lines which are the borders of said dividing line to said two ridgelines are each formed by a convex surface.

6. The dividable tablet of claim 1 or 2, wherein said dividing line is formed as a groove deeper than the upper surface of the peripheral portion of the tablet.

7. The dividable tablet of claim 3, wherein said dividing line is formed as a groove deeper than the upper surface of the peripheral portion of the tablet.

8. The dividable tablet of claim 4, wherein said dividing line is formed as a groove deeper than the upper surface of the peripheral portion of the tablet.

9. The dividable tablet of claim 5, wherein said dividing line is formed as a groove deeper than the upper surface of the peripheral portion of the tablet.

10. The dividable tablet of claim 4, wherein said dividing line is a v-shaped groove or a U-shaped groove.

11. The dividable tablet claim 10, wherein the lines which are the borders of the dividing line are formed at positions above the upper surface of the peripheral portion of the tablet.

12. The dividable tablet claim 11, wherein the areas from the two ridgelines to the peripheral portion of the tablet on the upper surface of the tablet are each a steep slope.

13. The dividable tablet of claim 12, wherein the steep slope has a plane surface or a convex surface when seen from side.

14. The dividable tablet of any one of claims 1 to 2, wherein areas around the points of intersection between said dividing line and the peripheral portions of the tablet are chamfered into two convex surfaces sandwiching said dividing line.

15. The dividable tablet of claim 3, wherein areas around the points of intersection between said dividing line and the peripheral portions of the tablet are chamfered into two convex surfaces sandwiching said dividing line.

16. The dividable tablet of claim 4, wherein areas around the points of intersection between said dividing line and the peripheral portions of the tablet are chamfered into two convex surfaces sandwiching said dividing line.

17. The dividable tablet of claim 4, wherein areas around the points of intersection between said dividing line and the peripheral portions of the tablet are chamfered into two convex surfaces sandwiching said dividing line.

18. A press-through pack containing dividable tablets according to any one of claims 1 or 2, comprising:

a storage body having a plurality of storage recessed portions interconnected by plate portions; and a sealing sheet having a base and an adhesive layer formed on one side of the base, said adhesive layer of said sealing sheet being bonded to said plate portions of said storage body to seal said storage body by said sealing sheet while respectively containing said dividable tablets in the plurality of said storage recessed portions of said storage body, said each of dividable tablets being able to be removed by breaking part of said sealing sheet sealing said storage recessed portions without the rise or peel-off of said sealing sheet at a bonding portion between said adhesive layer of said sealing sheet and said plate portion of said storage body when a projecting portion which is the exterior portion of said storage recessed portion containing said dividable tablets is pressed with a finger; and said sealing sheet being bonded to said plate portion of said storage body so that it can be easily separated from said storage body.

* * * * *

UNITED STATES PATENT AND TRADEMARK OFFICE
CERTIFICATE OF CORRECTION

PATENT NO. : 6,342,248 B1
DATED : January 29, 2002
INVENTOR(S) : Junichi Miyabe et al.

It is certified that error appears in the above-identified patent and that said Letters Patent is hereby corrected as shown below:

Column 1,
Line 29, "SA" should read -- Sa --.

Column 2,
Line 5, "twining)" should read -- twinning) --;
Line 13, "twining)" should read -- twinning) --;
Line 14, "easy" should read -- easily --;
Line 19, "twining" should read -- twinning --; and
Line 40, "twining" should read -- twinning --.

Column 3,
Line 2, "twining" should read -- twinning --.

Column 4,
Line 16, "twining" should read -- twinning --.

Column 6,
Line 14, "twining" should read -- twinning --;
Line 38, "pneumatically" should read -- pneumatic --; and
Line 65, "pneumatically" should read -- pneumatic --.

Column 7,
Line 32, "ridgeline" should read -- ridgelines --; and
Line 56, "twining" should read -- twinning --.

Column 16,
Line 34, "Large" should read -- large --.

Column 20,
Line 32, "(seethe" should read -- (see --.

Column 30,
Line 59, "twining" should read -- twinning --.

Column 32,
Line 26, "pneumatically" should read -- pneumatic --.

Column 33,
Line 9, "twining" should read -- twinning --.

UNITED STATES PATENT AND TRADEMARK OFFICE
CERTIFICATE OF CORRECTION

PATENT NO.   : 6,342,248 B1
DATED        : January 29, 2002
INVENTOR(S)  : Junichi Miyabe et al.

It is certified that error appears in the above-identified patent and that said Letters Patent is hereby corrected as shown below:

Column 35,
Line 17, "portion" should read -- portions --.

Column 36,
Line 1, "tablet" should read -- tablet of --;
Line 5, "tablet" should read -- tablet of --;
Line 10, "from side" should read -- from a side --; and
Line 11, "to" should read -- or --.

Signed and Sealed this

Third Day of September, 2002

Attest:

JAMES E. ROGAN
Attesting Officer    Director of the United States Patent and Trademark Office